United States Patent [19]
Lebouitz et al.

[11] Patent Number: 5,919,364
[45] Date of Patent: Jul. 6, 1999

[54] MICROFABRICATED FILTER AND SHELL CONSTRUCTED WITH A PERMEABLE MEMBRANE

[75] Inventors: Kyle S. Lebouitz, Albany; Roger T. Howe, Lafayette; Albert P. Pisano, Livermore, all of Calif.

[73] Assignee: Regents of the University of California, Oakland, Calif.

[21] Appl. No.: 08/669,149

[22] Filed: Jun. 24, 1996

[51] Int. Cl.⁶ .................................................. B01D 63/00
[52] U.S. Cl. .............................. 210/321.84; 210/500.25; 210/500.26; 210/483; 210/323.1
[58] Field of Search .................. 210/500.26, 200.25, 210/490, 321.75, 323.1, 483; 250/289, 288; 156/625.1; 237/233

[56] References Cited

U.S. PATENT DOCUMENTS

| | | | |
|---|---|---|---|
| 3,438,504 | 4/1969 | Furman | 210/483 |
| 4,941,893 | 7/1990 | Hsieh et al. | |
| 5,466,932 | 11/1995 | Young et al. | 250/289 |
| 5,589,136 | 12/1996 | Northrup et al. | 422/102 |
| 5,644,177 | 7/1997 | Guckel et al. | 310/40 |
| 5,659,171 | 8/1997 | Young et al. | 250/289 |

OTHER PUBLICATIONS

R. C. Anderson et al., "Formation, properties 'and applications of porous silicon," Ph.D. Thesis'Dept. of Chemical Engineering, U.C. Berkeley, Apr. 1991.

R. C. Anderson et al. "Porous polycrystalline silicon: a new material for MEMS," Journal of Microelectromechanical Systems, vol.3, No. 1, Mar. 1994, pp. 10–18.

T. J. Brosnihan et al., "Surface micromachined angular accelrometer with force feedback," *Proceedings of the ASME Dynamic Systems and Control Division,* San Francisco, California, USA, 1995, pp. 941–947.

D. W. Burns, Micromechanics of intergrated sensors and the planar processed pressure transducers, *Ph.D. Thesis,* Department of Material Science, University of W'sconsin, Madison, W'sconsin, USA, 1988.

(List continued on next page.)

*Primary Examiner*—Ana Fortuna
*Attorney, Agent, or Firm*—Fish & Richardson P.C.

[57] ABSTRACT

Microfabricated filters constructed with permeable polysilicon membranes and methods for fabricating such filters. The filters include a frame structure having a plurality of openings therethrough and a permeable polysilicon membrane disposed over the openings in the frame structure. The frame structure provides support for the permeable polysilicon membrane. The pores of the filter may be smaller than the resolution limit of photolithography. The width of the pores may be as small as about 0.01 $\mu$m, while the length of the pores may be as small as about 0.05 $\mu$m. The filters feature a relatively high throughput due to the extremely short pore length. The filters may be fabricated utilizing standard microfabrication processes. Also, microfabricated shells constructed with permeable membranes for encapsulating microfabricated devices such as microelectromechanical structures (MEMS) and methods for fabricating such shells. The shells include a frame structure having a plurality of openings therethrough, a permeable membrane disposed on the openings through the frame structure, an optional sealing structure disposed on the permeable membrane, and a cavity bounded by the frame structure. The frame structure provides support for the permeable membrane. The permeable membrane may be a thin film layer of polysilicon having a thickness of less than about 0.3 $\mu$m. The shells and methods for fabricating the shells minimize the damage incurred by the encapsulated microfabricated device during the fabrication of the shell without restricting the width of the shell. The shells may be fabricated utilizing standard microfabrication processes.

15 Claims, 15 Drawing Sheets

OTHER PUBLICATIONS

D. W. Burns et al., "A digital pressure sensor based on resonant microbeams," *Proceedings of thc Solid–State Sensor and Actuator Workshop*. Hilton Head, South Carolina, USA, Jun. 12–16, 1994, pp. 221–224.

Y. H. Cho et al., "Viscous energy dissipation in laterally oscillating planar microstructures: a theoretical and experimental study," *Proceedings of the IEEE Micro Electro Mechanical Systems Workshop (MEM93)*. 1993, pp. 93–98.

M. Chonko et al., "The integrity of very thin silicon films deposited on SI02," *The Physics and Chemistry of $SiO_2$ and the $Si$–$SiO_2$ Interface 2*. edited by: C. R. Helms and B. E. Deal, Plenum Press, New York, USA, 1993, 357–362.

L. A. Field, Fluid–Actuated Micromachined Rotors and Gears, *Ph.D. Thesis*. EECS Department, University of California Berkley, Berkeley, California, USA, 1991.

H. Guckel and D. W. Burns, "Planar processed polysilicon sealed cavities for pressure transducer arrays," *Pro–ceedings of the International Electron Devices Meeting*. Dec. 9–12, 1984, pp. 223–225.

H. Guckel et al., "The application of fine–grained, tensile polysilicon to mechanically resonant transducers," *Sensors and Actuators,* vol. A21–23, 1990, pp. 346–351.

H. Guckel et al., "Polysilicon resonant microbeam technology for high performance sensor applications," *Proceedings of the IEEE Solid–State Sensor and Actuator Workshop*. Hilton Head, South Carolina, USA, Jun. 21–24, 1992, pp. 153–156.

H. Guckel, et al. "Construction and performance characteristics of polysilicon resonating beam force transducers", *Elsevier Science Publishers*. pp. 393–404.

H. Guckel et al., "Fabrication techniques for integrated sensor microstructures," *IEDM,* (1986) pp. 176–179.

H. Guckel et al., "Laser–recrystallized piezoresistive micro–diaphragm sensor," *IEEE* (1995) pp. 182–185.

H. Guckel, "Structure micromachined presure transducers," *Elsevier Sequoia, Lausanne*. (1991) pp. 133–146.

K. Ikeda et al., "Three dimensional micromachining of silicon resonant strain gauge," *Digest of the 7th Sensor Symposium,* Tokyo, Japan, 1988, pp. 193–196.

K. Ikeda et al., "Silicon pressure sensor with resonant strain gauge built into diaphragm," *Digest of the 7th Sensor Symposium*. Tokyo, Japan, 1988, pp. 55–58.

K. Ikeda, et al., "Silicon pressure sensor integrates resonant strain gauge on diaphram," *Sensors and Actuators*. (1990), pp. 146–150.

K. Ikeda, et al., "Three–dimensional micromachining of silicon pressure sensor integrating resonant strain gauge on diaphram," *Sensors and Actuators*. (1990) pp. 1007–1010.

P. T. Jones, A Micro–Electro–Mechanical Systems (MEMS) Devices to Measure the Fracture Strain of Polycrystalline Silicon, M. S. *Thesis*. ME Department, University of California at Berkeley, Berkeley, California, USA, 1995.

M. W. Judy and R. T Howe, "Polysilicon hollow beam lateral resonators," *Proceedings of the IEEE Micro Electro Mechanical Systems Workshop*. Fort Lauderdale, Florida, USA, Feb. 1–10, 1993, pp. 265–271.

M. W. Judy, "Micromechanisms using sidewall beams," Ph.D. Thesis, EECS Dept., U.C. Berkeley, May 1994.

K S. Lebowitz et al., "Permeable polysilicon etch–access windows for microshell fabrication." In: 8th International Conference on Solid–State Sensors and Actuators and Eurosensors IX. Digest of Technical Papers (IEEE Cat. no.95TH8173). (8th International Conference on Solid–State Sensors and Actuators and Eurosensors IX. Digest of Technical Papers (IEEE Cat. No.95TH8173) Proceedings of the International Solid–State Sensors and Actuators Conference –Transducers '95, Stockholm, Sweden, Jun. 25–29, 1995). Sweden: Found. Sensors & Actuator Techol. 1995. pp. 224–227 vol. 1.

[18] R. Legtenberg and H. A. C. Tilmans, "Electrostatically driven vacuum–encapsulated polysilicon resonators. Part I: design and fabrication," *Sensors and Actuators*. vol. A45, 1994, kpp. 57–66.

L. Lin et al., "Silicon processed microneedles," *7th International Conference on Solid–State Sensors and Actuators (Transducers 93)*. Yokohama, Japan, Jun. 7–10, 1993, pp. 237–240.

L. Lin et al., "Vacuum–encapsulated lateral microresonators," *7th International Conference on Solid–State Sensors and Actuators (Transducers 93)*. Yokohama, Japan, Jun. 7–10, 1993, pp. 270–273.

L. Lin, Selective Encapsulation of MEMS: Micro Channels, Needles, Resonators and Electromechanical Filters, *Ph D. Thesis*. ME Department, University of California Berkeley, Berkeley, California, US~ Dec. 1993.

C. Liu et al., "Studies on the sealing of surface micromachined vacitires using chemical vapor deposition materials" *Electrical Engineering*. Jun. 1994, pp. 103–106.

C. H. Mastrangelo et al. "Vacuum–sealed silicon micromachined incandescent light source," *IEEE International Electron Devices Meeting*. San Francisco, California, USA, Dec., 1989, pp. 503–506.

D.J. Monk et al., "Hydrofluoric acid etching of silicon dioxide sacrificial layers. I. Experimental observations," *Journal of the Electrochemical Society*. vol. 141, 1994, pp. 264–274.

D. J. Monk et al., "Stress–corrosion cracking and blistering of thin polysilicon films in hydrofluoric acid" *Materials Research Society Symposium Proceedings*. vol. 308, San Francisco, California, USA, May 1993, pp. 641–646.

G. T. Mulhern et al., "Supercritical carbon dioxide drying of microstructures," *7th International Conference on Solid–State Sensors and Actuators (Transducers 93)*. Yokohama, Japan, Jun. 7–10, 1993, pp. 296–299.

C. T.–C. Nguyen et al., "Design and performance of CMOS micromechanical resonator oscillators," *Proceedings of the 1994 IEEE International Frequency Control Symposium*. Boston, Massachusetts, 1994, pp. 127–134.

T. A. Roessig et al., "Surfaee–micromachined resonant force sensor," *Proceedings of the ASME Dynamic Systems and Control Division*. San Francisco, California, USA, 1995, pp.871–876.

S. J. Sherman et al., Quinn, "A low cost monolithic accel-erometer;" *1992 Symposium on VLSI Circuits. Digest of Technical Papers*. Seattle, Washington, USA, Jun. 4–6, 1992, pp. 34–35.

J. J. Sniegowski, Design and fabrication of the polysilicon resonating beam force transducer, *Ph.D. Thesis*. EECS Department, University of Wisconsin, Madison, Wisconsin, USA, 1991.

W. C. Tang et al., "Laterally driven polysilicon resonant microstructures," *Sensors and Actuators*. vol. 20, 1989, pp. 25–32.

A. A. Uhlir, Jr., "Electrolytic shaping of germanium and silicon," Bell Systems Technical Journal, pp. 333–347, 1956.

C. J. M. van Rijn et al., "Microfiltration membrane sieve with silicon micromachining for industrial and biomedical applications," Proceedings. EKE Micro Electro Mechanical Systems 1995. Amsterdam, Netherlands, Jan. 29–Feb. 2. 1995. New York. NY. USA, 1995, pp. 83–87.

J. A. Walker et al., "Mechanical integrity of polysilicon films exposed to hydrofluoric acid solutions." *IEEE MEMS–90 Workshop.* Napa Valley, California, USA, Feb., 1990, pp. 56–60.

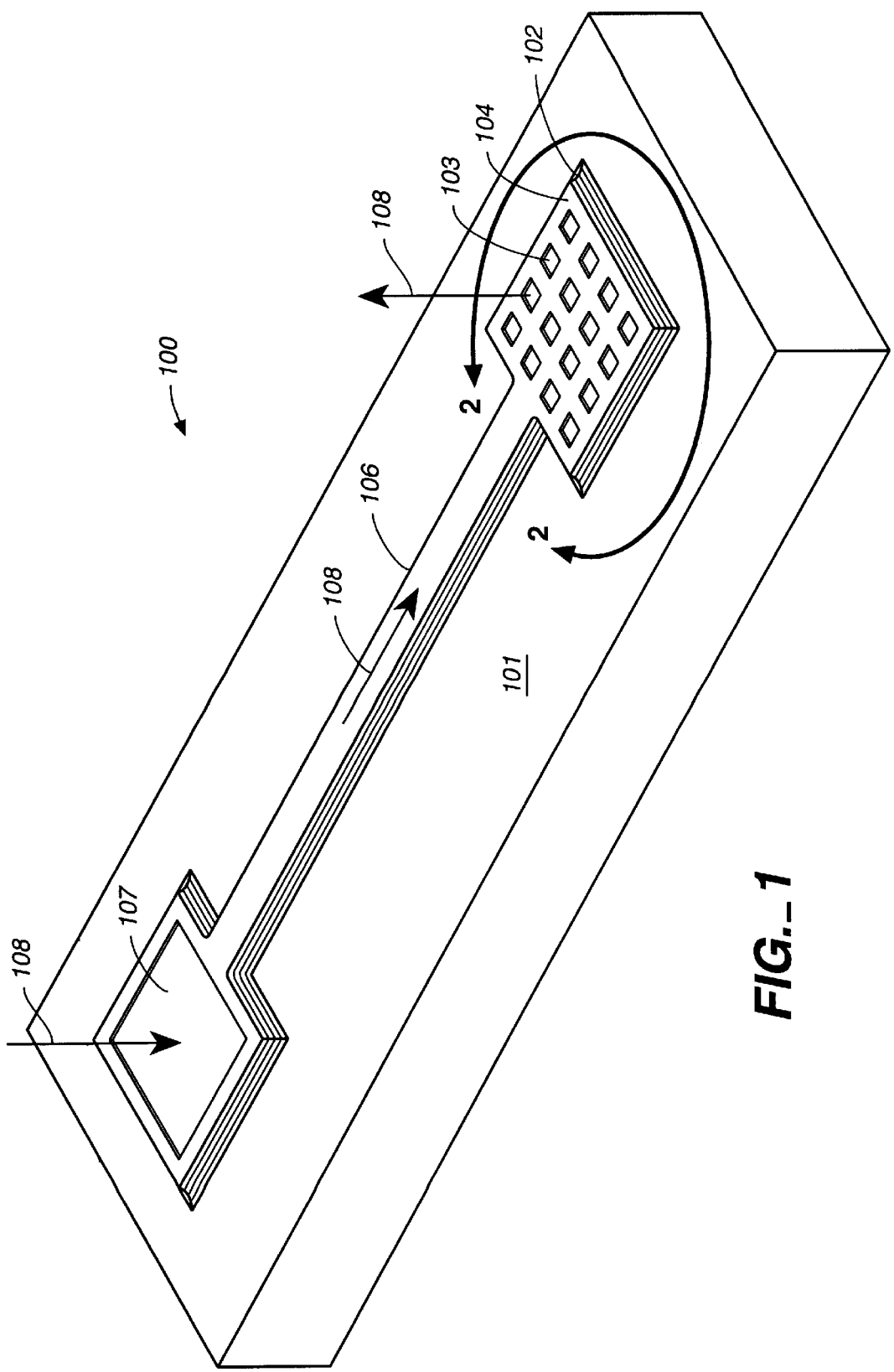
FIG._1

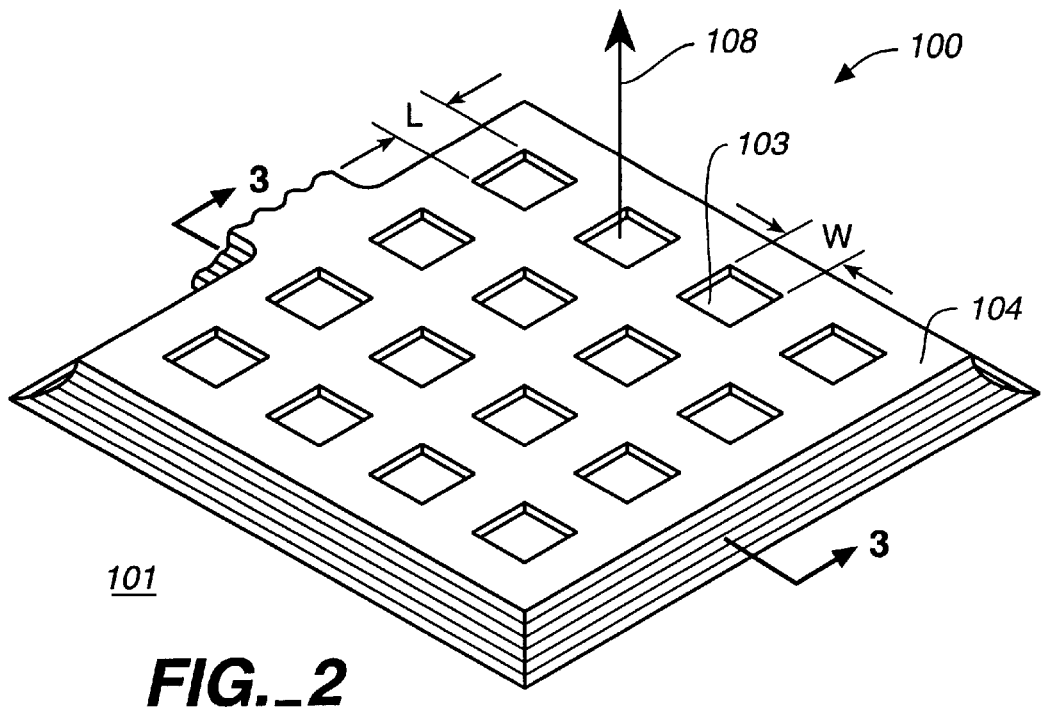
FIG._2
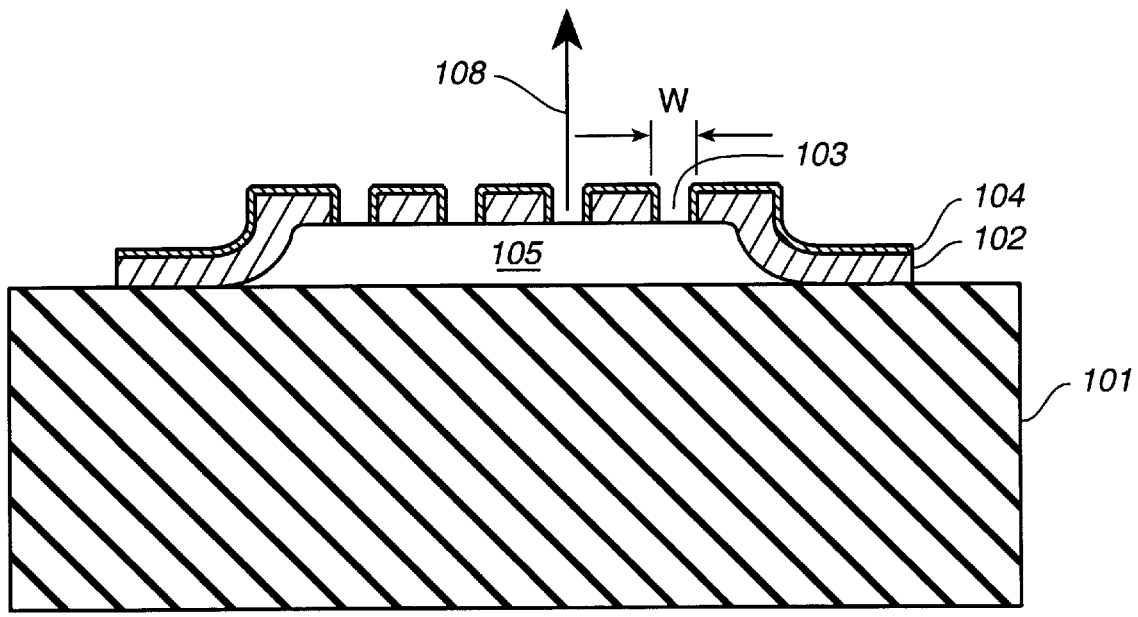
FIG._3

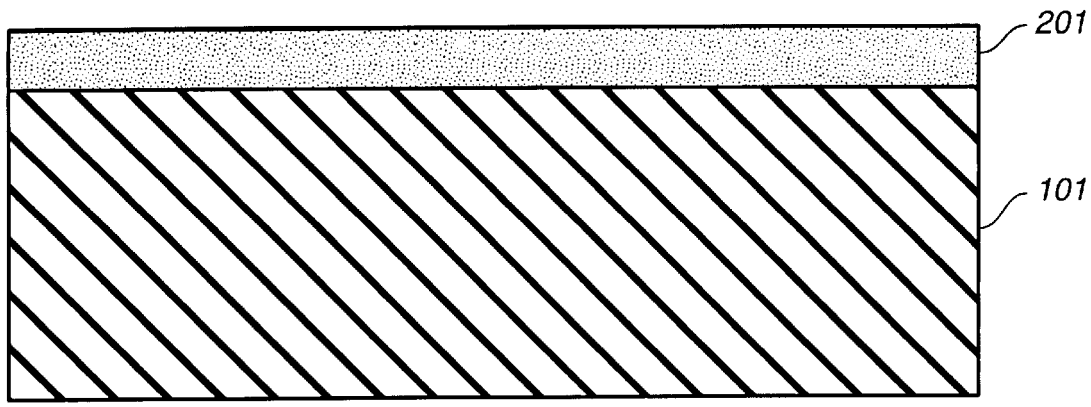
FIG._4
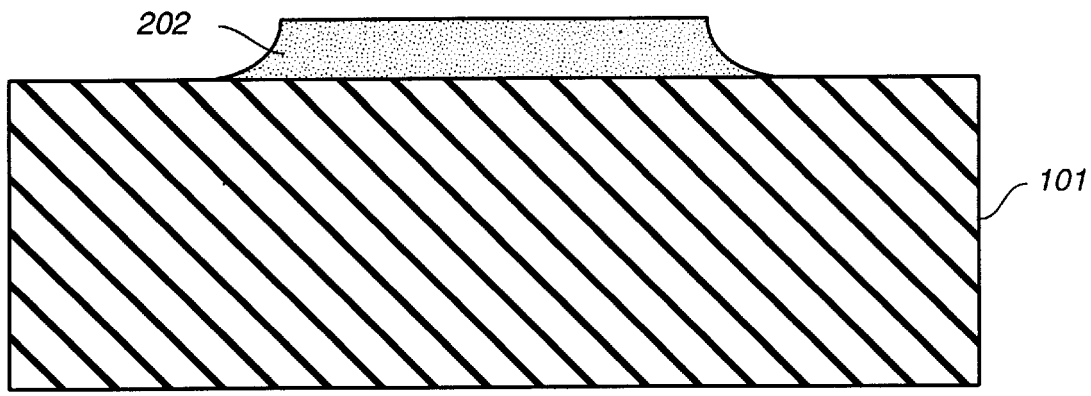
FIG._5
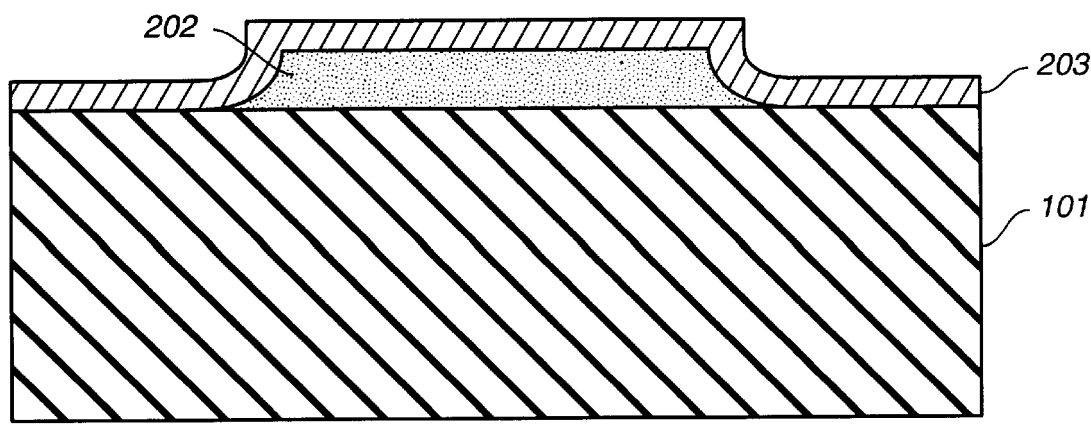
FIG._6

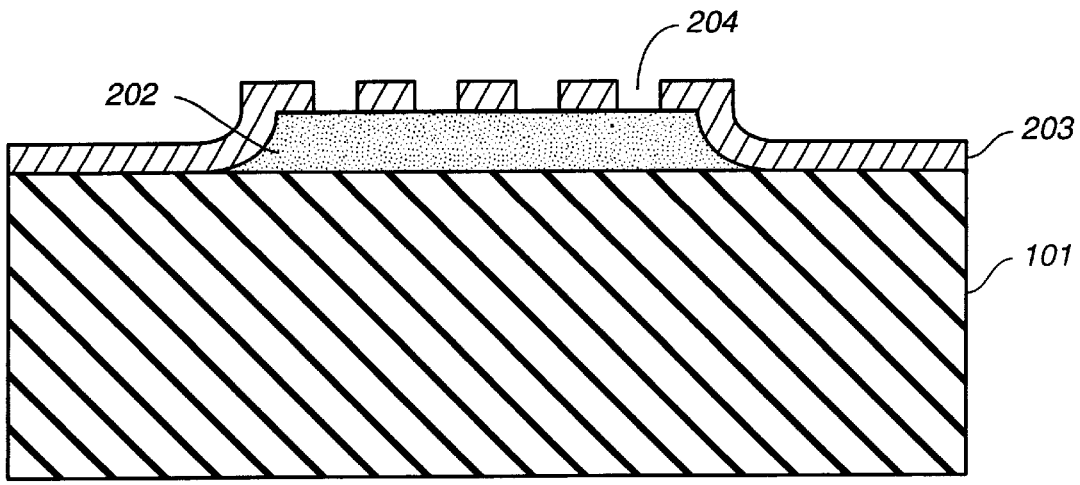
FIG._7
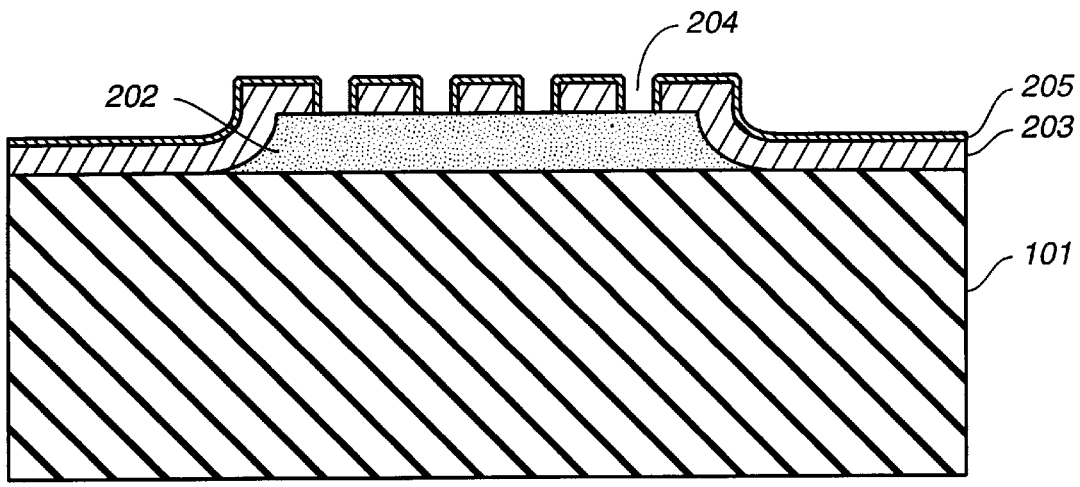
FIG._8
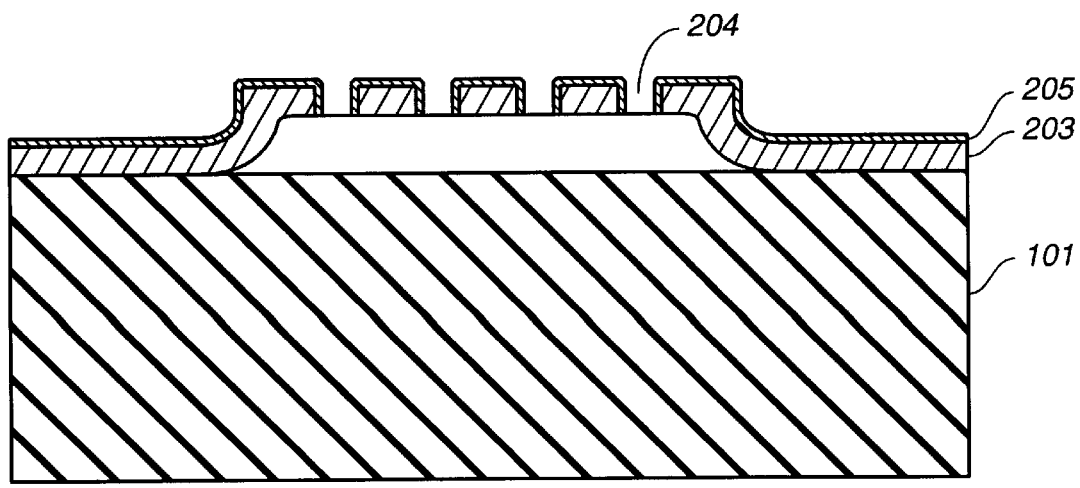
FIG._9

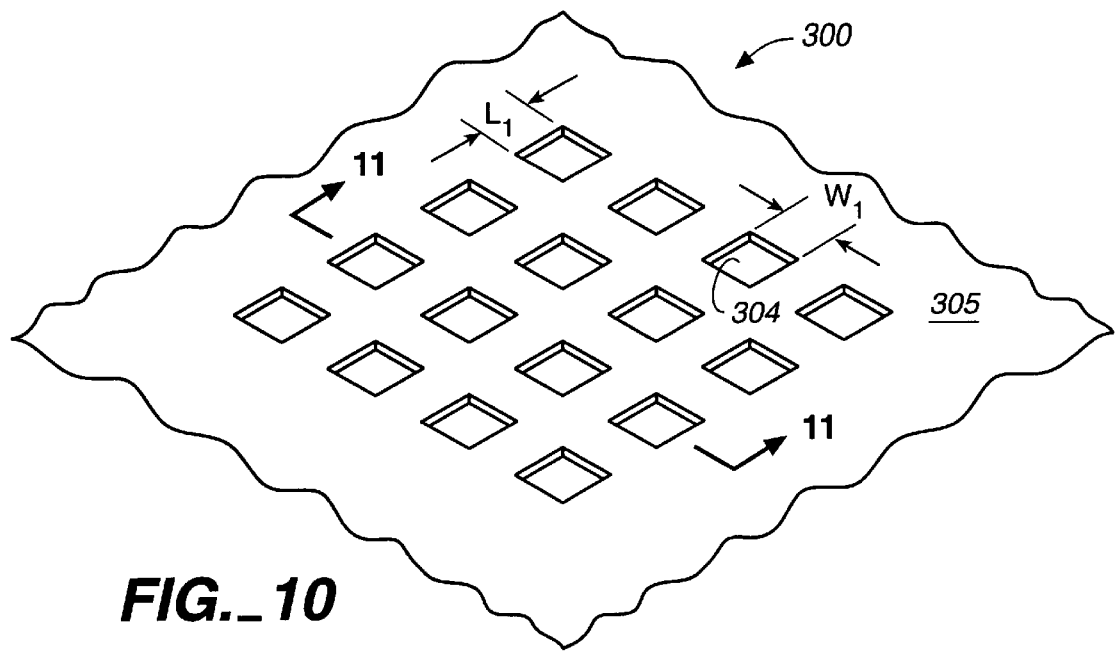
FIG._10
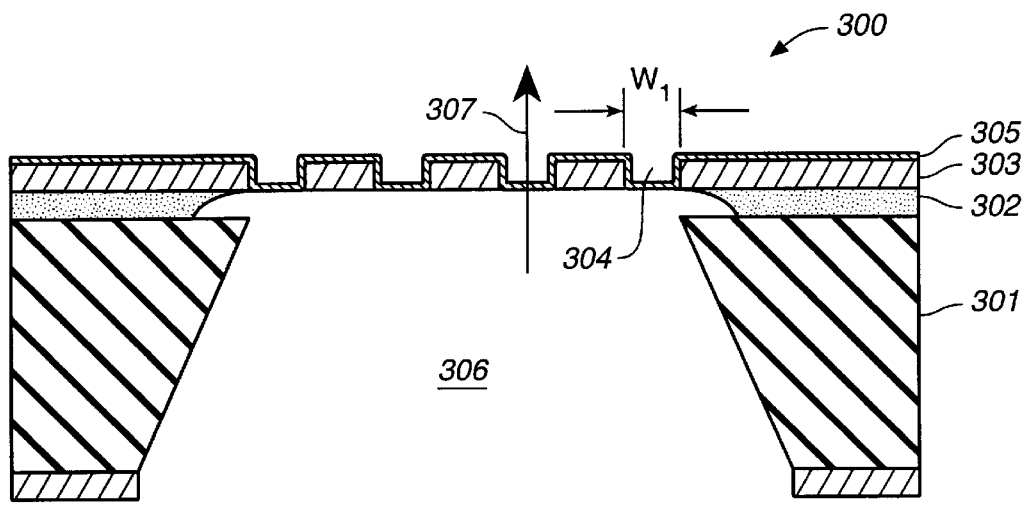
FIG._11

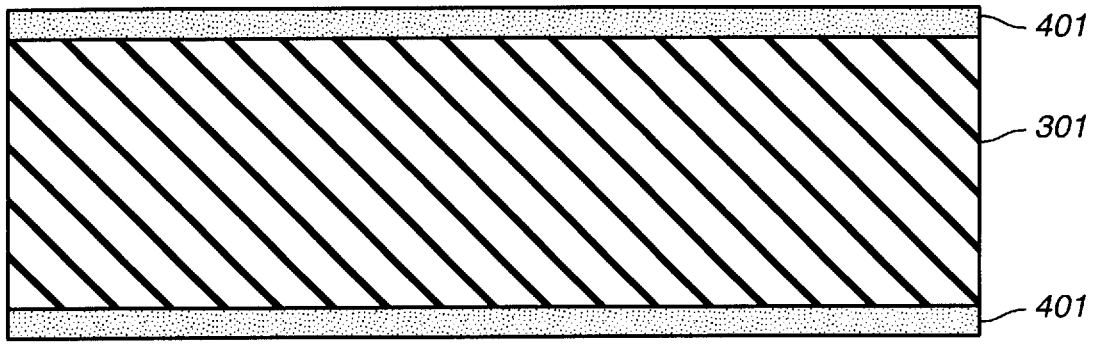
FIG._12
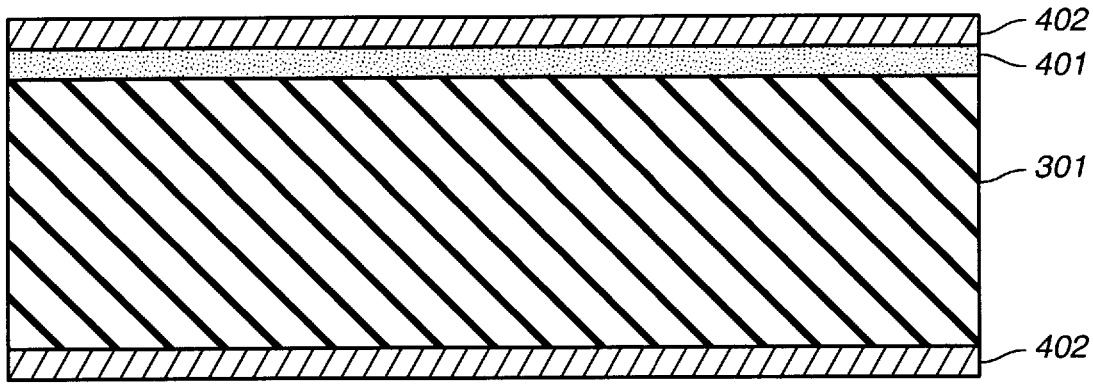
FIG._13
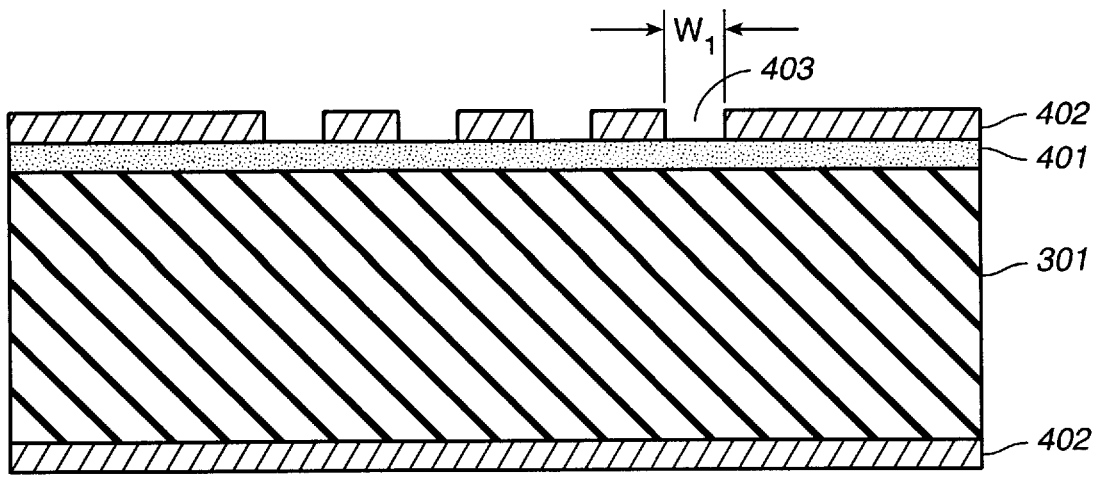
FIG._14

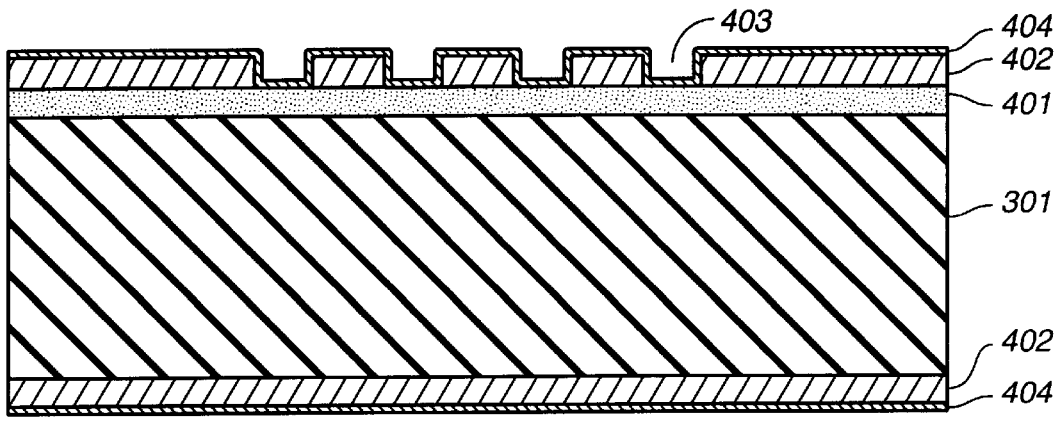
FIG._15
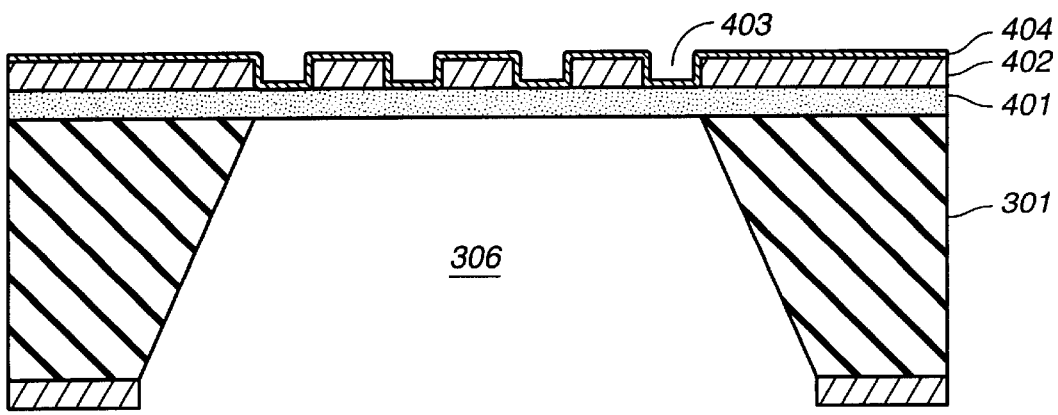
FIG._16
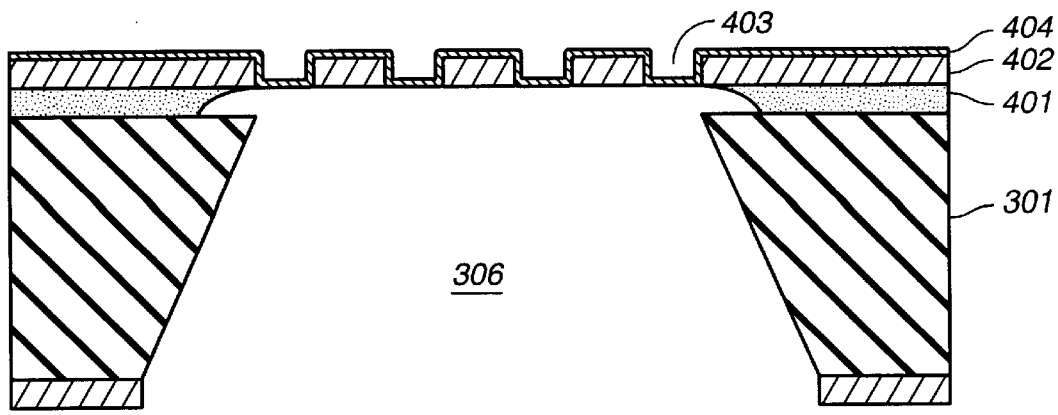
FIG._17

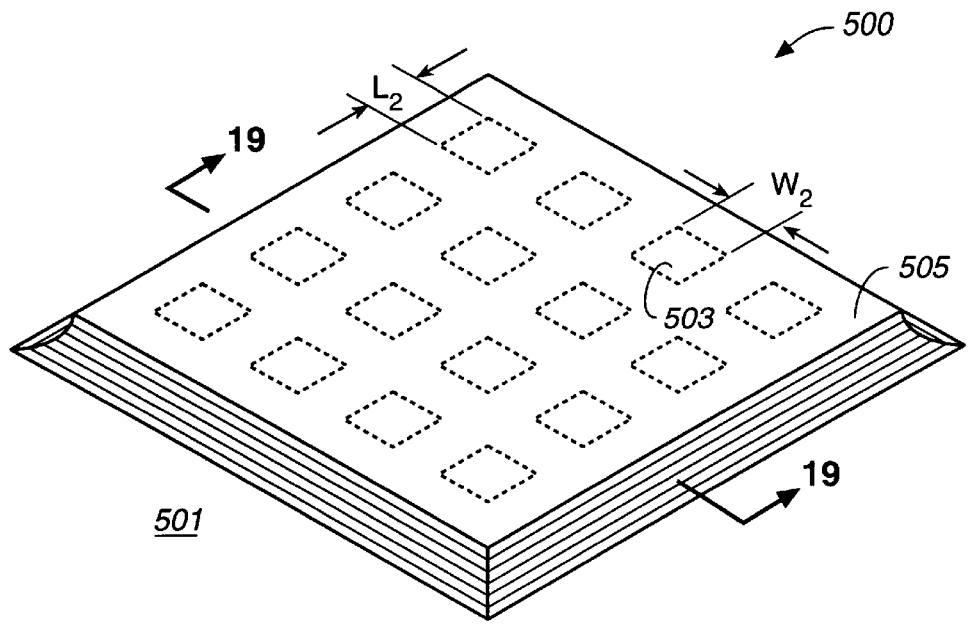
FIG._18
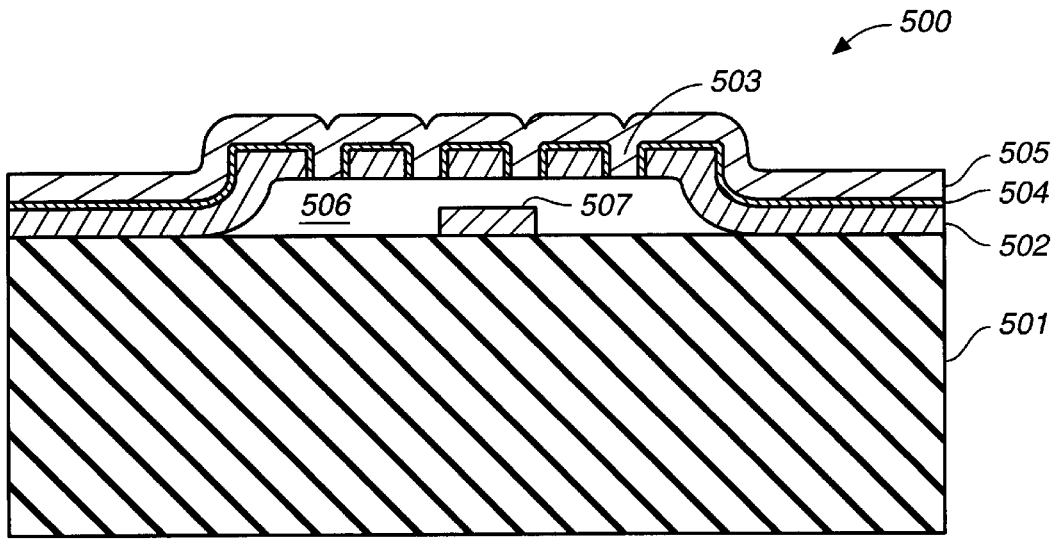
FIG._19

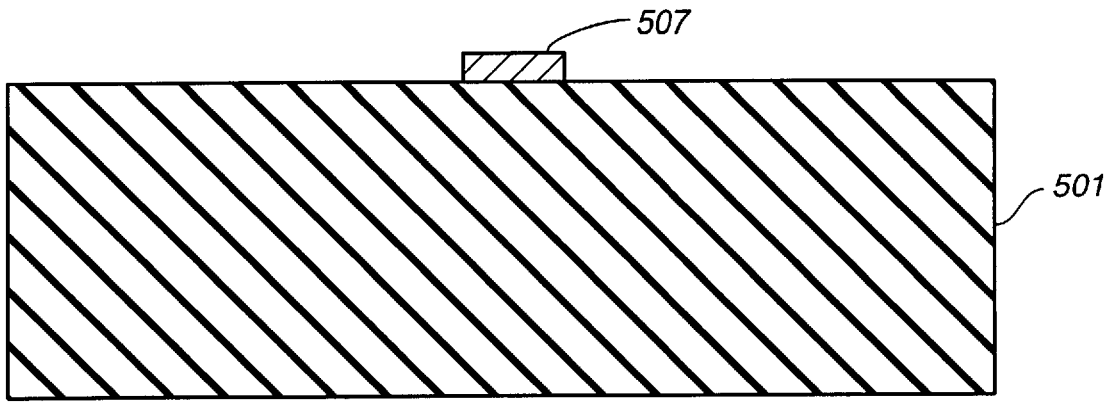
FIG._20
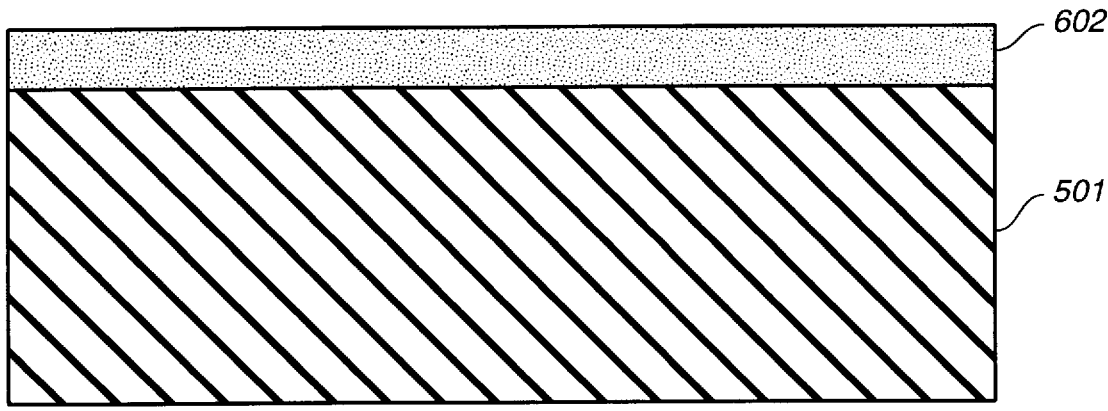
FIG._21
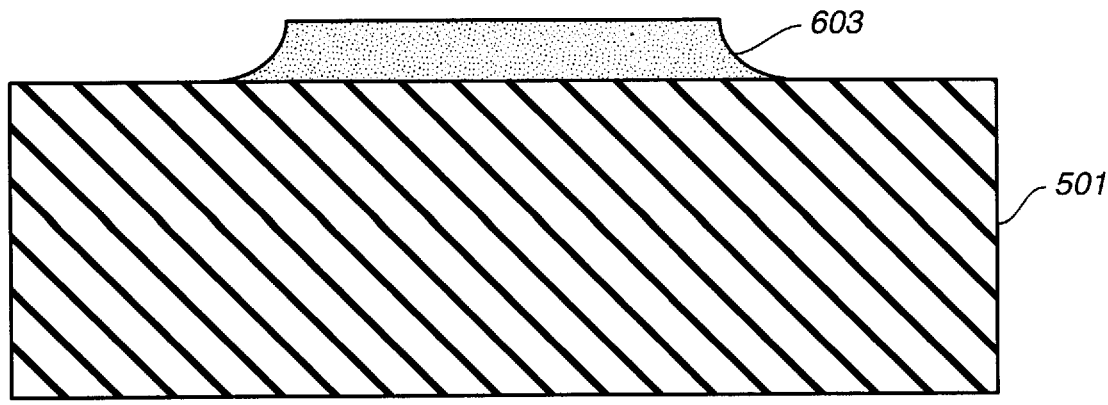
FIG._22

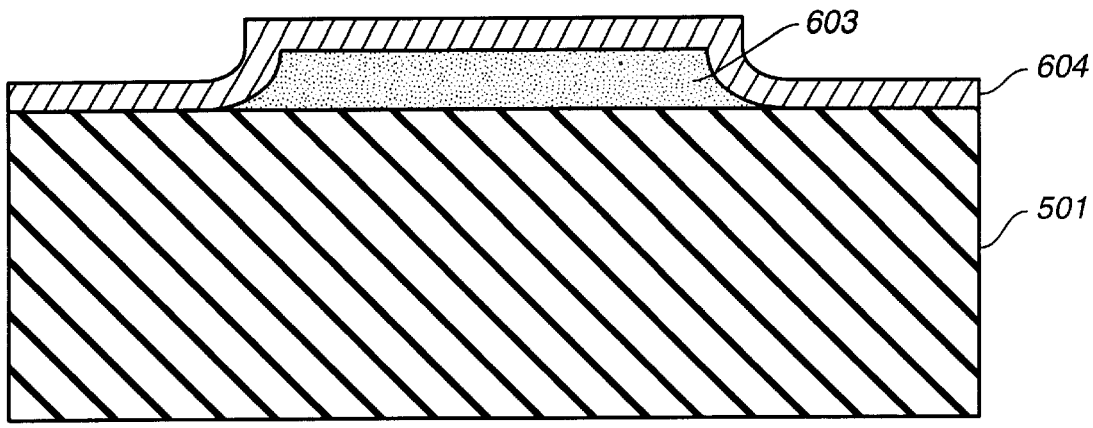
FIG._23
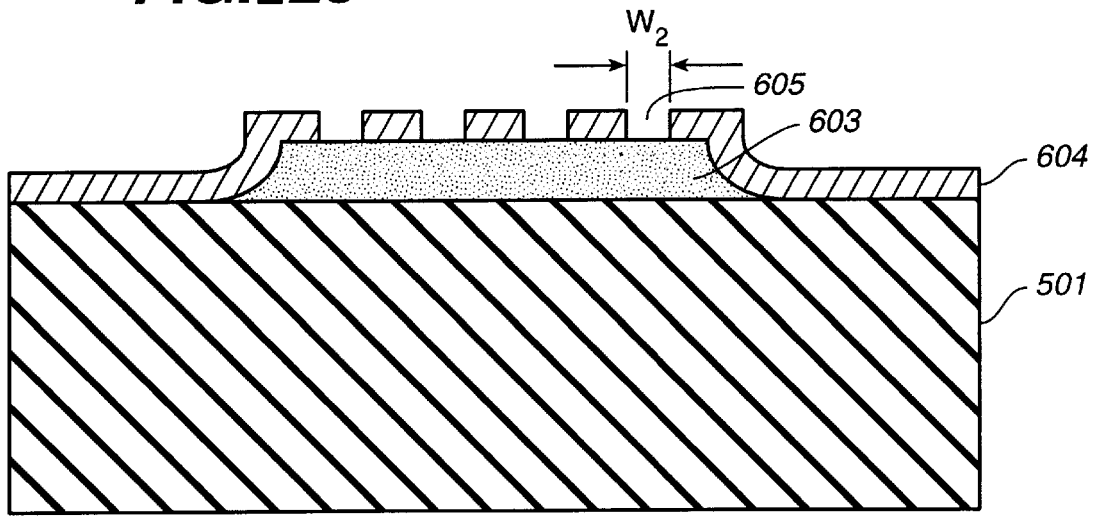
FIG._24
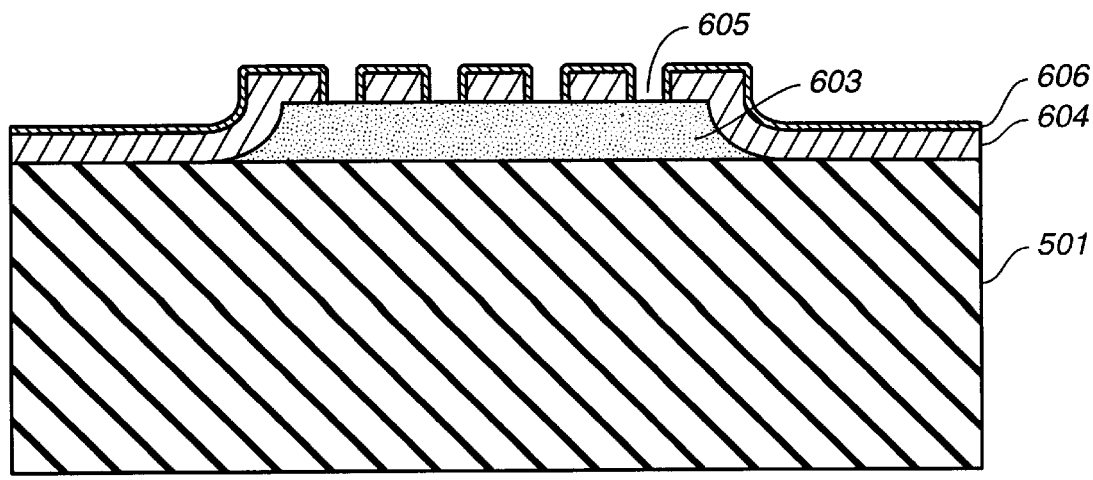
FIG._25

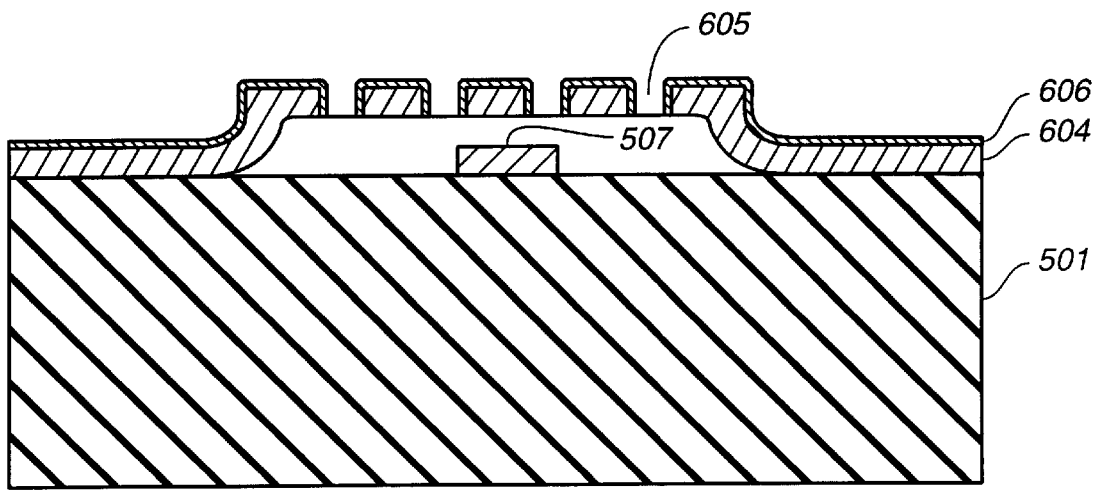
FIG._26
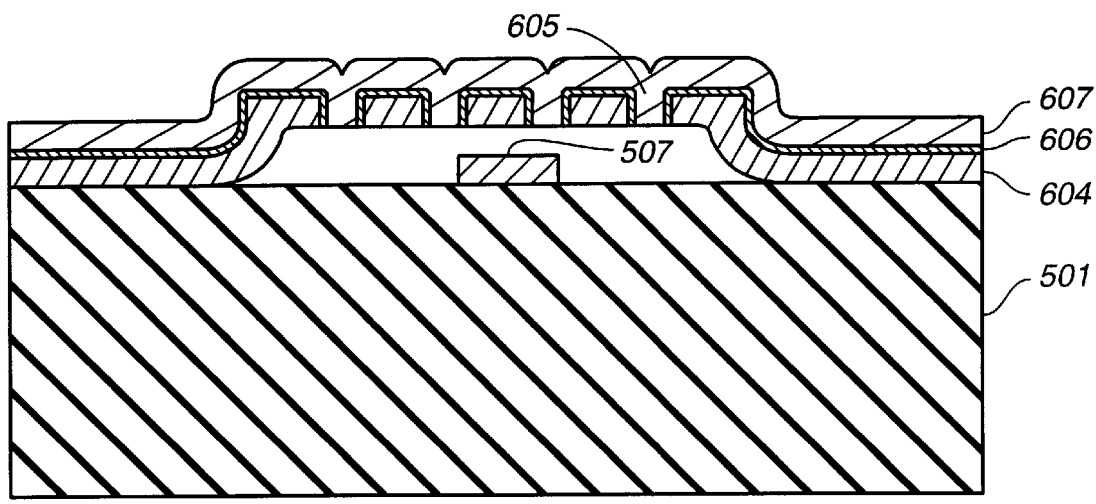
FIG._27

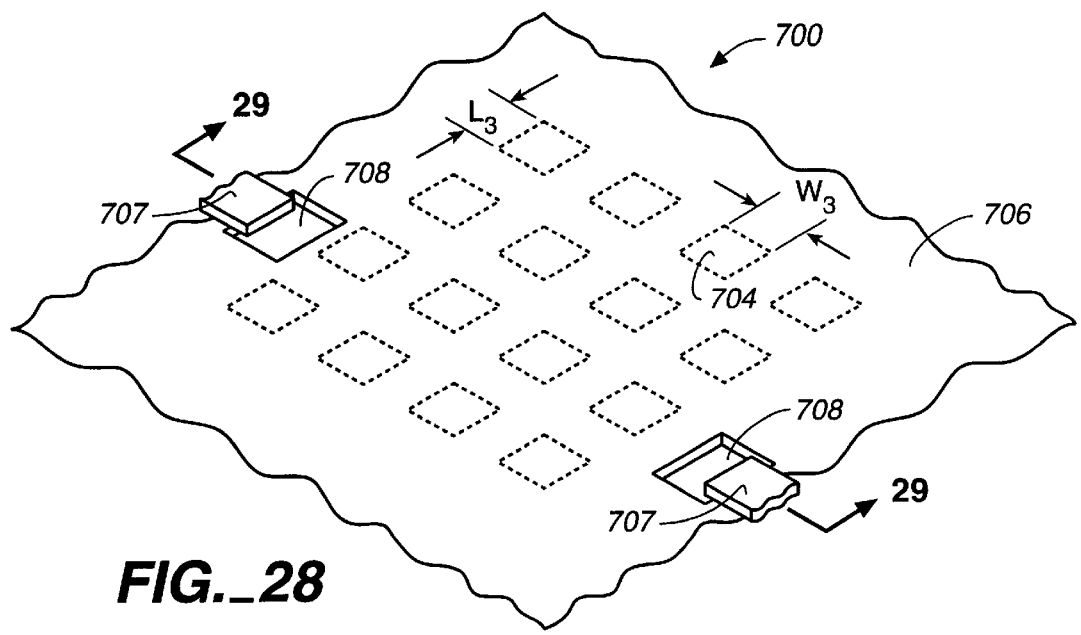
FIG._28
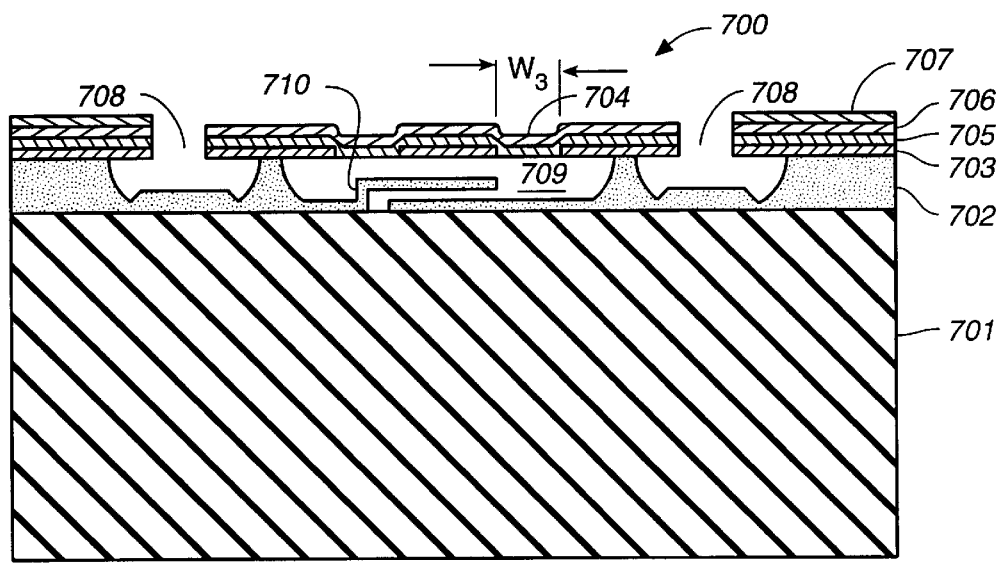
FIG._29

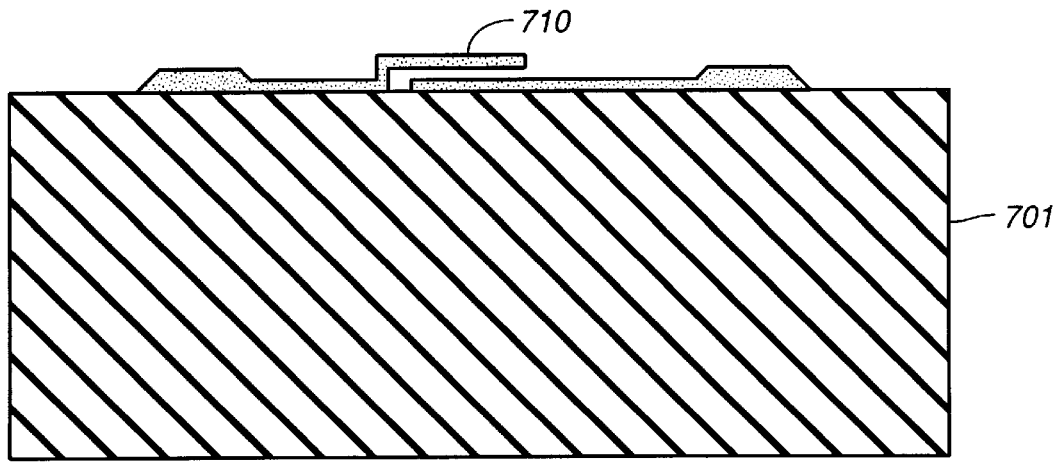
FIG._30
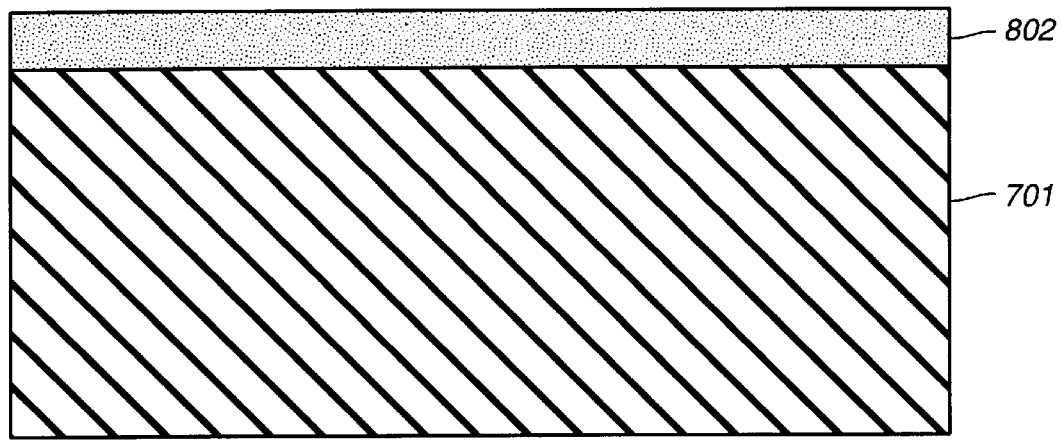
FIG._31
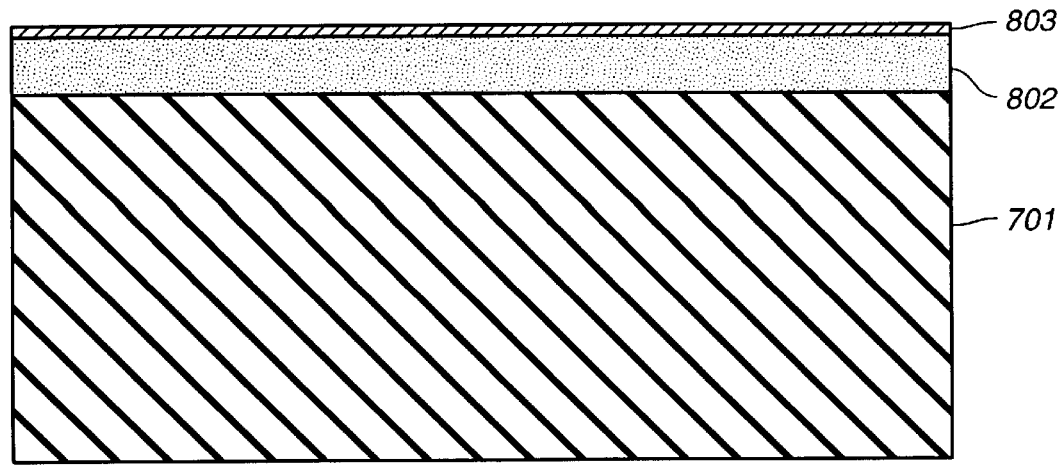
FIG._32

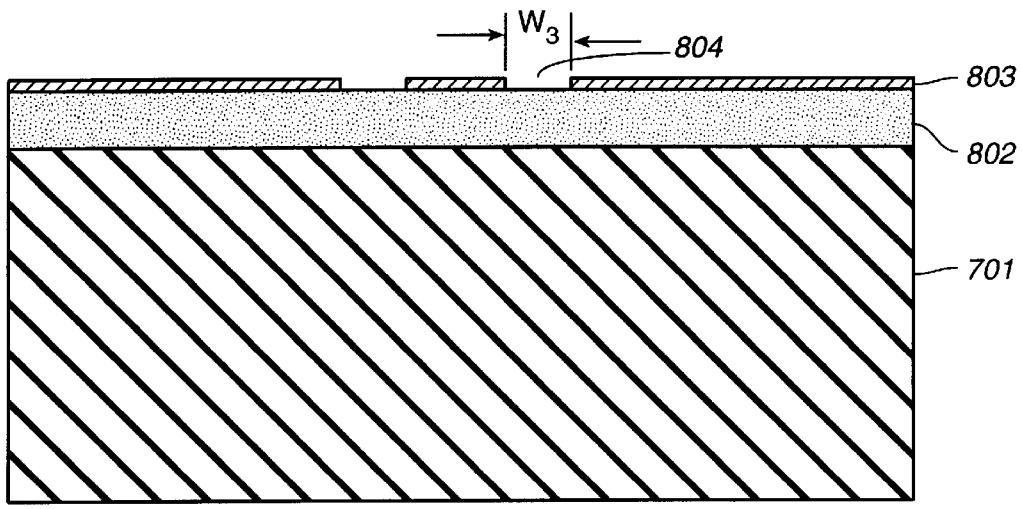
FIG._33
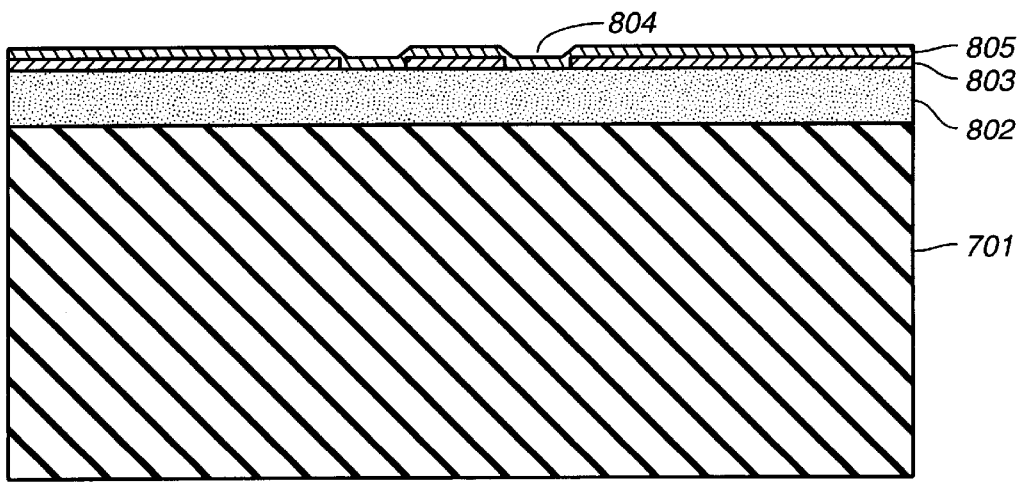
FIG._34
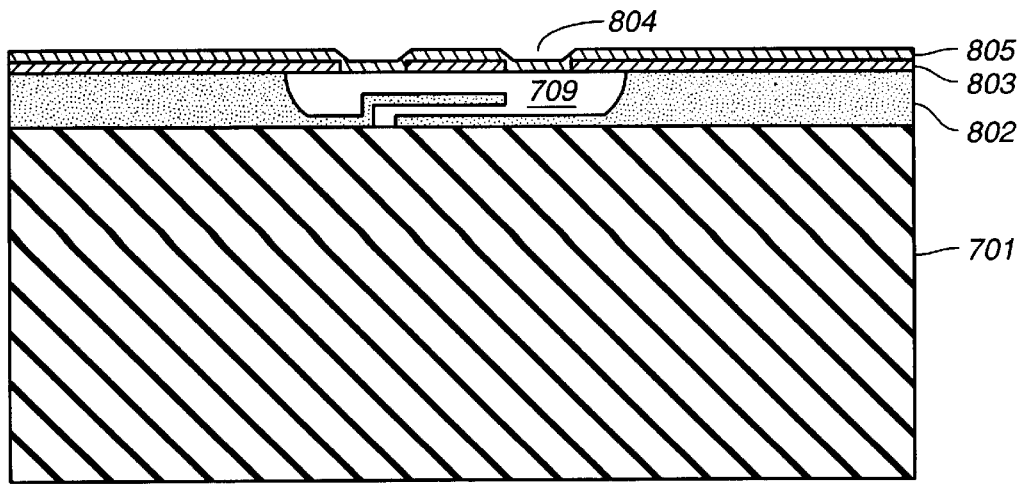
FIG._35

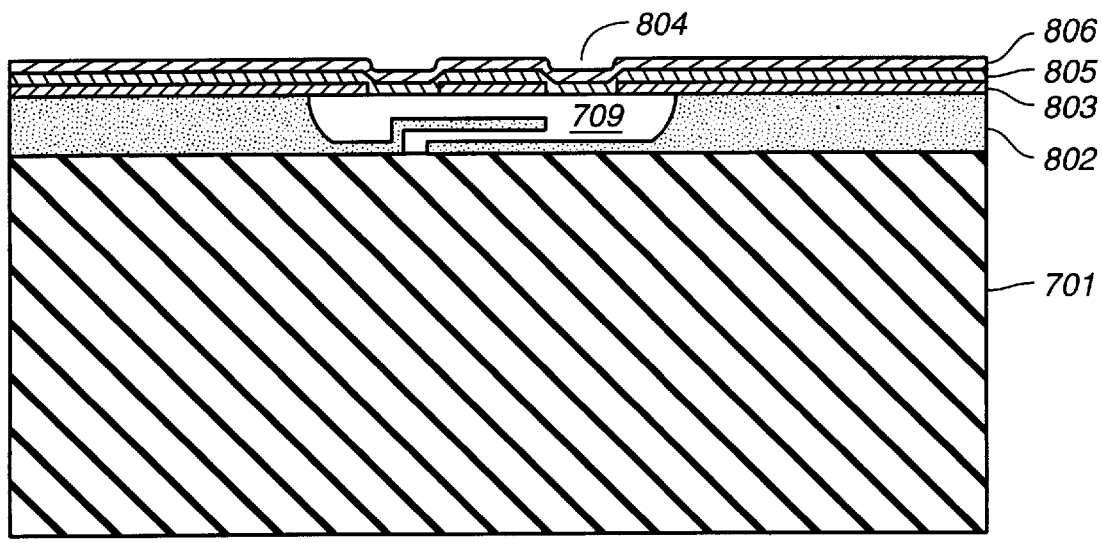
FIG._36
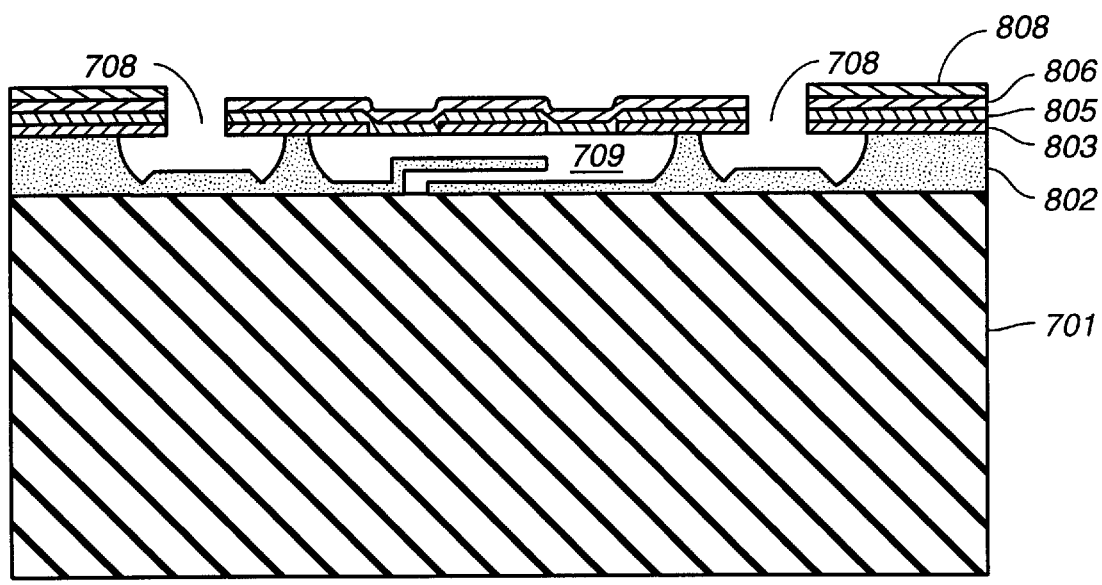
FIG._37

MICROFABRICATED FILTER AND SHELL CONSTRUCTED WITH A PERMEABLE MEMBRANE

BACKGROUND OF THE INVENTION

The present invention relates generally to filtration devices and more particularly to microfabricated filters constructed with permeable membranes. The present invention further relates to microfabricated shells constructed with such membranes for encapsulating microfabricated devices such as microelectromechanical structures (MEMS).

Filtration devices are extensively used in industrial applications, such as within the biomedical industry, for separating particles of specific sizes from a fluid. For these applications, required filtration device features typically include: relatively uniform pore sizes and distributions, pore sizes as small as the nanometer (nm) range, high throughput, and adequate mechanical strength.

Filter pore sizes in the nanometer range would allow biologically-important molecules to be mechanically separated on the basis of size. For instance, such pore sizes may be used to achieve the heretofore elusive goal of viral elimination from biological fluids.

Filters constructed with porous materials are known in the art. For instance, a porous polycrystalline silicon (polysilicon) plug for use as a filter is described by Anderson in "Formation, Properties, and Applications of Porous Silicon," Ph.D. Thesis, Dept. of Chemical Engineering, U.C. Berkeley, April 1991, and summarized in "Porous Polycrystalline Silicon: A New Material for MEMS," Journal of Microelectromechanical Systems, Vol. 3, No. 1, March 1994, pp. 10–18. The porous polysilicon plug is formed by depositing a layer of polysilicon on a substrate using low-pressure chemical vapor deposition (LPCVD) and then etching the polysilicon layer with an electrochemical anodization process to make it porous. The porous polysilicon provides pore features of about 0.3 micrometers ($\mu$m) in width. The electrochemical etching process, however, requires an anodization apparatus, which is not typically used in standard microfabrication processes. Furthermore, the porous polysilicon plug is permeable only in a planar direction with respect to the substrate.

The permeability of thin layers (less than about 0.3 $\mu$m thick) of polysilicon to hydrofluoric (HF) acid has been discussed by Judy et al. in "Polysilicon Hollow Beam Lateral Resonators," *Proceedings of the IEEE Micro Electromechanical Systems Workshop*, Fort Lauderdale, Fla., Feb. 1–10, 1993, pp. 265–71; by Monk et al. in "Stress-corrosion Cracking and Blistering of Thin Polysilicon Films in Hydrofluoric Acid," *Materials Research Society Symposium Proceedings*, Vol. 308, San Francisco, Calif., May 1993, pp. 641–6; and by Chonko et al. in "The Integrity of Very Thin Silicon Films Deposited on $SiO_x$," *The Physics and Chemistry of $SiO_S$ and the Si—$SiO_S$ Interface* 2, edited by C. R. Helms, Plenum Press, New York, 1993, pp. 357–62. However, these references are not directed to the use of thin layers of polysilicon as filters.

Microfabricated shells are used to encapsulate microfabricated devices such as MEMS. MEMS include devices such as micro-resonators and inertial sensors. The shells provide a hermetic, low-pressure environment that is essential for achieving a high quality (Q) factor and low Brownian noise in the operation of MEMS.

Microfabricated shells may be fabricated by etching a sacrificial layer disposed beneath a frame layer, thus forming a cavity, as described by Lin in "Selective Encapsulation of MEMS: Micro Channels, Needles, Resonators and Electromechanical Filters," Ph.D. Thesis, ME Department, University of California, Berkeley, Berkeley, Calif., December 1993. In this technique, etch holes are formed through the frame layer to allow an etchant to pass into the shell and etch the sacrificial layer. The etch holes are subsequently closed to hermetically seal the shell by depositing a sealant over the frame layer.

The etch holes are placed around the perimeter of the frame layer to minimize the amount of sealant passing through the etch holes and depositing on the encapsulated microfabricated device. Deposition of sealing film on the microfabricated device is undesirable since it may alter the device's characteristics. However, this placement of the etch holes increases the time required to etch the sacrificial layer due to the increased distance the etch is required to travel to remove the sacrificial layer. Long etch times are undesirable since long-term exposure to hydrofluoric acid is damaging to polysilicon structures which may be present in the microfabricated device. As a result, the width of shells must be limited in order to keep the etch times reasonable.

The use of permeable polysilicon for fabricating microfabricated shells is mentioned by Judy in "Micromechanisms Using Sidewall Beams," Ph.D. Thesis, EECS Dept., U.C. Berkeley, May 1994 and by Lin in his 1993 Ph.D. Thesis mentioned above. However, neither reference discloses any details of a structure or fabrication process for incorporating permeable polysilicon in such shells.

Accordingly, it is an object of the present invention to provide filters having a pore width as small as the nanometer range, yet also having a pore length as small as the tenths of a micrometer range to maximize throughput.

An additional object of the present invention is to provide filters that have a high mechanical strength.

A further object of the present invention is to provide methods for the construction of such filters using standard microfabrication processes.

Another object of the present invention is to provide shells that minimize the damage incurred by the encapsulated microfabricated device during the fabrication of the shell without restricting the width of the shell.

Yet another object of the present invention is to provide methods for the construction of such a shell.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to microfabricated filters and methods for fabricating such filters. The present invention is further directed to microfabricated shells constructed with permeable membranes for encapsulating microfabricated devices such as MEMS and methods for fabricating such shells.

The microfabricated filters include a frame structure having a plurality of openings therethrough. A permeable polysilicon membrane is disposed over the openings in the frame structure. The frame layer provides support for the permeable polysilicon membrane, thus improving the mechanical strength of the filter. The plurality of openings in the frame structure may be distributed over the surface of the frame structure.

The construction of such microfabricated filters may begin with a bulk substrate. A sacrificial structure is then formed over the bulk substrate to define a cavity. Next, a frame structure having a plurality of openings is formed over at least part of the sacrificial structure and the bulk substrate. A permeable polysilicon structure is then formed over at least part of the frame structure. Finally, the sacrificial structure is removed with an etchant. The permeable polysilicon structure allows the etchant to pass through the openings in the frame layer and etch the sacrificial structure, thus forming the cavity.

The pores of the microfabricated filters are defined by the structure of the permeable polysilicon membrane. As a result, the width and length of the pores may be smaller than the resolution limit of photolithography. The width of the pores may be as small as about 0.01 $\mu$m, while the length of the pores may be as small as about 0.05 $\mu$m.

The filters feature a high throughput due to the extremely short pore length. The filters also provide a relatively high mechanical strength due to the support of the permeable membrane by the frame structure. The filters may be constructed utilizing standard microfabrication processes.

The shells of the present invention are comprised of a bulk substrate, a frame structure having a plurality of openings therethrough disposed on the bulk substrate, a permeable membrane disposed on the openings through the frame structure, a sealing structure disposed on the permeable membrane, and a cavity bounded by the bulk substrate and the frame structure. Optionally, a microfabricated device may be disposed within the cavity. The frame layer provides support for the permeable membrane, thus improving the mechanical strength of the shell. The plurality of openings in the frame structure may be distributed over the surface of the frame structure to maximize the etch rate of a sacrificial layer used to define the cavity. The sealing structure hermetically seals the shell and may be omitted if the shell is intended for filtration purposes. The permeable membrane may be a thin film layer of polysilicon having a thickness of less than about 0.3 $\mu$m.

The construction of such microfabricated shells may begin with a bulk substrate. A sacrificial structure is then formed over the bulk substrate to define a cavity. Next, a frame structure having a plurality of openings is formed over at least part of the sacrificial structure and the bulk substrate. A permeable membrane is then formed over at least part of the frame structure. Next, the sacrificial structure is removed by passing an etchant through the permeable membrane, thus forming the cavity. A sealing layer is then formed over the frame layer and openings, thus hermetically sealing the shell. The sealing layer may be omitted if the shell is intended for filtration purposes.

The shells and methods for fabricating the shells minimize the damage incurred by the encapsulated microfabricated device during the fabrication of the shell without restricting the size of the shell. The permeable membrane allows the etchant to enter the shell while blocking passage of the sealing layer. As a result, the openings in the frame structure may be distributed over the surface of the frame layer to maximize the etch rate of the sacrificial structure without causing the deposition of the sealing layer on the microfabricated device. The shells may be fabricated utilizing standard microfabrication processes.

BRIEF DESCRIPTION OF THE DRAWINGS

The accompanying drawings, which are incorporated in and constitute a part of the specification, schematically illustrate the present invention and, together with the general description given above and the detailed description given below, serve to explain the principles of the invention.

FIG. 1 is a perspective view of a filter in accordance with the present invention.

FIG. 2 is an enlarged perspective view of the circled area of FIG. 1.

FIG. 3 is a cross-sectional view along line 3—3 of FIG. 2.

FIGS. 4–9 are cross-sectional views illustrating the steps in the fabrication of the filter of FIG. 1.

FIG. 10 is a perspective view of an alternative embodiment of a filter in accordance with the present invention.

FIG. 11 is a cross-sectional view along line 11—11 of FIG. 10.

FIGS. 12–17 are cross-sectional views illustrating the steps in the fabrication of the filter of FIG. 10.

FIG. 18 is a perspective view of a shell in accordance with the present invention.

FIG. 19 is a cross-sectional view along line 19—19 of FIG. 18.

FIGS. 20–27 are cross-sectional views illustrating the steps in the fabrication of the shell of FIG. 18.

FIG. 28 is a perspective view of an alternative embodiment of a shell in accordance with the present invention.

FIG. 29 is a cross-sectional view along line 29—29 of FIG. 28.

FIGS. 30–37 are cross-sectional views illustrating the steps in the fabrication of the shell of FIG. 28.

DESCRIPTION OF THE REPRESENTATIVE EMBODIMENTS

The present invention is directed to microfabricated filters and shells constructed with permeable membranes and methods for fabricating such filters and shells. The present invention will be described in terms of several representative embodiments.

A filter 100 in accordance with the present invention is shown in FIGS. 1, 2 and 3. The filter may be used for separating particles of specific sizes from a fluid.

Referring to FIGS. 1, 2 and 3, filter 100 includes a bulk substrate 101, a frame structure 102 having a plurality of openings 103 therethrough disposed over the bulk substrate, a permeable polysilicon membrane 104 disposed over the frame structure, a cavity 105 bounded by the bulk substrate and the frame structure, a channel 106, and an inlet/outlet port 107. The plurality of openings 103 may be distributed over the surface of frame structure 102. Openings 103 may, for instance, be square in shape and range from about 0.3 $\mu$m to about 600 $\mu$m in width (W) and length (L). To achieve the desired permeability characteristics, the thickness of the permeable polysilicon membrane should be less than about 0.3 $\mu$m and may be as small as about 0.05 $\mu$m.

The flow of fluid through the filter is indicated by arrows 108. The fluid flow may also occur in the direction opposite to that indicated.

Referring to FIG. 4, fabrication of filter 100 may begin with planar bulk substrate 101 such as a single crystalline <100>-silicon wafer. A sacrificial layer 201 is then deposited on the substrate using LPCVD. The sacrificial layer may be, for instance, a 5 $\mu$m-thick layer of phosphosilicate glass (PSG) containing 8 wt % phosphorus. The PSG may be deposited, for instance, using a temperature of 450° C., a pressure of 300 mTorr, a flow rate of 60 sccm of silane gas (SiH$_4$), 90 sccm of oxygen gas (O$_2$), and 10.3 sccm of phosphene gas (PH$_3$) for 1.5 hours.

Next, sacrificial layer 201 may be densified by placing bulk substrate 101 in, for instance, a nitrogen (N$_2$) environment at 950° C. for 1 hour.

Referring to FIG. 5, sacrificial layer 201 is then photolithographically patterned and isotropically etched to form mold 202. The etch may be performed using, for instance, a 5:1 buffered HF acid solution at 27° C. for about 3 minutes. Mold 202 is used to define the shape of cavity 105, channel 106, and inlet/outlet port 107 of filter 100 that are formed in subsequent steps of the process.

Next, referring to FIG. 6, a frame layer 203 is deposited over mold 202 and bulk substrate 101 using LPCVD. The frame layer may be, for instance, a 1 $\mu$m-thick layer of low-stress silicon nitride (SiN). The process parameters for the deposition may be, for instance: 835° C., 140 mTorr, 100 sccm dichlorosilane (DCS), and 25 sccm ammonia gas (NH$_3$), 4 hours.

Referring to FIG. 7, a plurality of openings 204 are then photolithographically defined and plasma etched through frame layer 203. Openings 204 may, for instance, be square in shape and have a width (W) ranging from about 0.3 $\mu$m to about 600 $\mu$m. The plasma etch may be performed, for instance, with a SF$_6$ plasma at a chamber pressure of 150 mTorr, a radio-frequency (RF) power of 200 Watts, and a gas flow rate of 80 sccm for 10 minutes. Frame layer 203 with openings 204 form frame structure 102 of filter 100. An additional opening (not shown) may also be etched through frame layer 203 to begin formation of inlet/outlet port 107 of filter 100.

Next, referring to FIG. 8, a permeable polysilicon layer 205 is deposited over frame layer 203 and openings 204 using a thin film deposition process, such as LPCVD. To achieve the desired permeability characteristics, the thickness of the permeable polysilicon layer should be less than about 0.3 $\mu$m and may be as small as about 0.05 $\mu$m. The process parameters for the deposition may be, for instance: 605° C., 555 mTorr, 125 sccm SiH$_4$, and 15 minutes, forming a permeable polysilicon layer about 0.1 $\mu$m thick. Permeable polysilicon layer 205 forms permeable polysilicon membrane 104 of filter 100.

Permeable polysilicon layer 205 may then be annealed by placing bulk substrate 101 in, for instance, an N$_2$ environment at 950° C. for 1 hour.

Next, referring to FIG. 9, mold 202 is removed using an etchant. The etchant passes through permeable polysilicon layer 205 in openings 204 to etch mold 202. The etch may, for instance, be performed with concentrated HF acid at 27° C. for 2 minutes. This etching step forms cavity 105, channel 106, and inlet/outlet port 107 of filter 100.

The processed substrate 101 is then rinsed in deionized (DI) water to remove all remaining HF acid. The rinse may be performed, for instance, for two hours.

Finally, the processed substrate 101 is dried using, for example, a super-critical carbon dioxide (CO$_2$) process. This process is selected to prevent the permeable polysilicon layer from cracking during drying.

A filter 300, which is an alternative embodiment of the present invention, is shown in FIGS. 10 and 11. Filter 300 includes a bulk substrate 301, a sacrificial structure 302 disposed over the bulk substrate, a frame structure 303 having a plurality of openings 304 therethrough disposed over the sacrificial structure, a permeable polysilicon membrane 305 disposed over the frame structure, and an inlet/outlet port 306. The plurality of openings 304 may be distributed over the surface of frame structure 303. openings 304 may, for instance, be square in shape and range from about 0.3 $\mu$m to about 600 $\mu$m in width (W$_1$) and length (L$_1$). To achieve the desired permeability characteristics, the permeable polysilicon membrane should be less than about 0.3 $\mu$m in thickness and may be as thin as about 0.05 $\mu$m.

The flow of fluid through the filter is indicated by arrow 307. The fluid flow may also occur in the direction opposite to that indicated.

Referring to FIG. 12, fabrication of filter 300 may begin with planar bulk substrate 301 such as a single crystalline <100>-silicon wafer. A sacrificial layer 401 is then deposited on the substrate using LPCVD. The sacrificial layer may be, for instance, a 5 $\mu$m-thick layer of phosphosilicate glass (PSG) containing 8 wt % phosphorus. The PSG may be deposited, for instance, using the following parameters: 450° C., 300 mTorr, 60 sccm SiH$_4$, 90 sccm O$_2$, 10.3 sccm PH$_3$, and 1.5 hours.

Next, sacrificial layer 401 may be densified by placing bulk substrate 301 in, for instance, an N$_2$ environment at 950° C. for 1 hour.

Referring to FIG. 13, a frame layer 402 is then deposited over sacrificial layer 401 using LPCVD. The frame layer may be, for instance, a 1 $\mu$m-thick layer of low-stress SiN. The process parameters for the deposition may be, for instance: 835° C., 140 mTorr, 100 sccm DCS, 25 sccm NH$_3$, and 4 hours.

Next, referring to FIG. 14, a plurality of openings 403 are photolithographically defined and plasma etched through frame layer 402. Openings 403 may, for instance, be square in shape and have a width (W$_1$) ranging from about 0.3 $\mu$m to about 600 $\mu$m. The plasma etch may be performed, for instance, with a SF$_6$ plasma at a chamber pressure of 150 mTorr, an RF power of 200 Watts, and a gas flow rate of 80 sccm for 10 minutes. Frame layer 402 with openings 403 form frame structure 303 of filter 300.

Referring to FIG. 15, a permeable polysilicon layer 404 is then deposited over frame layer 402 and openings 403 using a thin film deposition process, such as LPCVD. To achieve the desired permeability characteristics, the thickness of the permeable polysilicon layer should be less than about 0.3 $\mu$m and may be as small as about 0.05 $\mu$m. The process parameters for the deposition may be, for instance: 605° C., 555 mTorr, 125 sccm SiH$_4$, and 15 minutes, forming a permeable polysilicon layer about 0.1 $\mu$m thick. Permeable polysilicon layer 404 forms permeable polysilicon membrane 305 of filter 300.

Next, permeable polysilicon layer 404 may be annealed by placing bulk substrate 301 in, for instance, an N$_2$ environment at 950° C. for 1 hour.

Referring to FIG. 16, inlet/outlet port 306 is then formed by photolithographically patterning and anisotropically etching the backside of substrate 301 through to sacrificial layer 401. The etch may be performed, for instance, using ethylene diamine pyrocathecol (EDP) at 110° C. for 10 hours.

Next, referring to FIG. 17, sacrificial layer 401 is then partially removed using an etchant. The etchant passes through permeable polysilicon layer 404 in openings 403 and through inlet/outlet port 306 to etch sacrificial layer 401. The etch may, for instance, be performed with concentrated HF acid at 27° C. for 2 minutes. This etching step exposes permeable polysilicon layer 404 to inlet/outlet port 306, thus enabling fluid to flow through filter 300.

The processed substrate 301 is then rinsed in DI water to remove all remaining HF acid. The rinse may be performed, for instance, for two hours.

Finally, the processed substrate 301 is dried using, for example, a super-critical $CO_2$ process. This process is selected to prevent the permeable polysilicon layer from cracking during drying.

Combinations of materials different from those described above may be used to fabricate filters 100 and 200. For instance, sacrificial layers 201 and 401 may be composed of low-temperature oxide (LTO), frame layers 203 and 402 may be composed of undoped polysilicon, and permeable polysilicon layers 205 and 404 may be composed of in-situ doped polysilicon.

A shell 500 in accordance with the present invention is shown in FIGS. 18 and 19. The shell may be used to encapsulate a microfabricated device such as a MEMS. MEMS include devices such as micromachined resonators (microresonators) and inertial sensors. The shell may be used to provide a hermetic seal or alternatively, as a filter which selectively allows the passage of particles into the shell based on their size.

Referring to FIGS. 18 and 19, shell 500 includes a bulk substrate 501, a frame structure 502 having a plurality of openings 503 therethrough disposed over the bulk substrate, a permeable membrane 504 disposed over the frame structure, a sealing structure 505 disposed over the permeable membrane, a cavity 506 bounded by the bulk substrate and frame structure, and an optional nicrofabricated device 507 disposed within the cavity. The microfabricated device may be, for instance, a MEMS. The plurality of openings 503 may be distributed over the surface of frame structure 502. Openings 503 may, for instance, be square in shape and range from about 0.3 $\mu$m to about 600 $\mu$m in width ($W_2$) and length ($L_2$). Permeable membrane 504 may be a thin film composed of polysilicon. To achieve the desired permeability characteristics, the thickness of the permeable polysilicon membrane should be less than about 0.3 $\mu$m and may be as small as about 0.05 $\mu$m. Sealing structure 505 hermetically seals the shell and may be omitted if the shell is intended for filtration purposes.

Referring to FIG. 20, fabrication of shell 500 may begin with planar bulk substrate 501 such as a single crystalline <100>-silicon wafer. Next, microfabricated device 507, such as a microresonator, may optionally be formed on substrate 501 by processes commonly known in the art.

Referring to FIG. 21, a sacrificial layer 602 is then deposited over the substrate and the microfabricated device using LPCVD. The sacrificial layer may be, for instance, a 5 $\mu$m-thick layer of phosphosilicate glass (PSG) containing 8 wt % phosphorus. The PSG may be deposited, for instance, using the following parameters: 450° C., 300 mTorr, 60 sccm $SiH_4$, 90 sccm $O_2$, 10.3 sccm $PH_3$, and 1.5 hours.

Next, sacrificial layer 602 may be densified by placing bulk substrate 501 in, for instance, an $N_2$ environment at 950° C. for 1 hour.

Referring to FIG. 22, sacrificial layer 602 is then photolithographically patterned and isotropically etched to form mold 603. The etch may be performed using, for instance, a 5:1 buffered HF acid solution at 27° C. for 3 minutes. Mold 603 is used to define the shape of cavity 506 of filter 500 that is formed in subsequent steps of the process.

Next, referring to FIG. 23, a frame layer 604 is deposited over mold 603 and bulk substrate 501 using LPCVD. The frame layer may be, for instance, a 1 $\mu$m-thick layer of low-stress SiN. The process parameters for the deposition may be, for instance: 835° C., 140 mTorr, 100 sccm DCS, 25 sccm $NH_3$, and 4 hours.

Referring to FIG. 24, a plurality of openings 605 are then photolithographically defined and plasma etched through frame layer 604. Openings 605 may, for instance, be square in shape and have a width ($W_2$) ranging from about 0.3 $\mu$m to about 600 $\mu$m. The plasma etch may be performed, for instance, with a $SF_6$ plasma at a chamber pressure of 150 mTorr, an RF power of 200 Watts, and a gas flow rate of 80 sccm for 10 minutes. Frame layer 604 with openings 605 form frame structure 502 of shell 500.

Next, referring to FIG. 25, a permeable layer 606 is deposited over frame layer 604 and openings 605 using LPCVD. The permeable layer may, for instance, be a thin film of polysilicon. To achieve the desired permeability characteristics, the thickness of the permeable polysilicon layer should be less than about 0.3 $\mu$m and may be as small as about 0.05 $\mu$m. The process parameters for the deposition may be, for instance: 605° C., 555 mTorr, 125 sccm $SiH_4$, and 15 minutes, forming a permeable polysilicon layer about 0.1 $\mu$m thick. Permeable layer 606 forms permeable membrane 504 of shell 500.

Permeable layer 606 may then be annealed by placing bulk substrate 501 in, for instance, an $N_2$ environment at 950° C. for 1 hour.

Next, referring to FIG. 26, mold 603 is then removed using an etchant. The etchant passes through permeable layer 606 in openings 605 to etch mold 603. The etch may, for instance, be performed with concentrated HP acid at 27° C. for 2 minutes. This etching step forms cavity 506 of shell 500.

The processed substrate 501 is then rinsed in DI water to remove all remaining HF acid. The rinse may be performed, for instance, for two hours.

Next, the processed substrate 501 is dried using, for example, a super-critical $CO_2$ process. This process is selected to prevent the permeable layer from cracking during drying.

Finally, referring to FIG. 27, a sealing layer 607 is deposited over permeable layer 606 using LPCVD. The sealing layer may be, for instance, a 0.8 $\mu$m-thick layer of low-stress SiN. The process parameters for the deposition may be, for instance, 835° C., 140 mTorr, 100 sccm DCS, and 25 sccm $NH_3$. This step forms sealing structure 505 of shell 500 and may be omitted if the shell is intended for use as a filter rather than as a hermetic seal.

A shell 700, which is an alternative embodiment of the present invention, is shown in FIGS. 28 and 29. Shell 700 includes a bulk substrate 701; a sacrificial structure 702 disposed over the bulk substrate; a frame structure 703 having a plurality of openings 704 therethrough disposed over the sacrificial structure; a permeable membrane 705 disposed over the frame structure; a sealing structure 706 disposed over the permeable polysilicon membrane; a plurality of openings 708 disposed through the frame structure, permeable polysilicon membrane, and sealing layer; and a cavity 709 bounded by the bulk substrate and the frame structure. Optionally, shell 700 may include a metallization layer 707 disposed over the sealing structure and a microfabricated device 710 disposed within the cavity. The microfabricated device may be, for instance, a microresonator. Openings 704 may be distributed over the surface of frame structure 703. Openings 704 may be square in shape and range from about 0.3 $\mu$m to about 600 $\mu$m in width ($W_3$) and length ($L_3$). Permeable membrane 705 may be a thin film composed of polysilicon. To achieve the desired permeability characteristics, the thickness of the permeable polysilicon membrane should be less than about 0.3 $\mu$m and may be as small as about 0.05 $\mu$m. Sealing structure 706 hermetically seals the shell and may be omitted if the shell is intended for filtration purposes. Metallization layer 707 may be used to form external electrical connections to microfabricated device 710 through openings 708.

Referring to FIG. 30, fabrication of shell 700 may begin with planar bulk substrate 701 such as a single crystalline <100>-silicon wafer. Next, microfabricated device 710 may be formed on substrate 701 by processes commonly known in the art.

Referring to FIG. 31, a sacrificial layer 802 is then deposited over the substrate and the microfabricated device using LPCVD. The sacrificial layer may be, for instance, a 5 $\mu$m-thick layer of phosphosilicate glass (PSG) containing 8 wt % phosphorus. The PSG may be deposited, for instance, using the following parameters: 450° C., 300 mTorr, 60 sccm $SiH_4$, 90 sccm $O_2$, 10.3 sccm $PH_3$, and 1.5 hours.

Next, sacrificial layer 802 may be densified by placing bulk substrate 701 in, for instance, an $N_2$ environment at 950° C. for 1 hour.

Referring to FIG. 32, a frame layer 803 is then deposited over sacrificial layer 802 using LPCVD. The frame layer may be, for instance, a 1 $\mu$m-thick layer of low-stress SiN. The process parameters for the deposition may be, for instance: 835° C., 140 mTorr, 100 sccm DCS, 25 sccm $NH_3$, and 4 hours.

Referring to FIG. 33, a plurality of openings 804 are then photolithographically defined and plasma etched through frame layer 803. Openings 804 may, for instance, be square in shape and have a width ($W_3$) ranging from about 0.3 $\mu$m to about 600 $\mu$m. The plasma etch may be performed, for instance, with a $SF_6$ plasma at a chamber pressure of 150 mTorr, an RF power of 200 Watts, and a gas flow rate of 80 sccm for 10 minutes. Frame layer 803 with openings 804 form frame structure 703 of shell 700.

Next, referring to FIG. 34, a permeable layer 805 is deposited over frame layer 803 and openings 804 using LPCVD. The permeable layer may, for instance, be a thin film of polysilicon. To achieve the desired permeability characteristics, the thickness of the permeable polysilicon layer should be less than about 0.3 $\mu$m and may be as small as about 0.05 $\mu$m. The process parameters for the deposition may be, for instance: 605° C., 555 mTorr, 125 sccm $SiH_4$, and 15 minutes, forming a permeable polysilicon layer about 0.1 $\mu$m thick. Permeable polysilicon layer 805 forms permeable polysilicon membrane 705 of shell 700.

Permeable layer 805 is then annealed by placing bulk substrate 701 in, for instance, an $N_2$ environment at 950° C. for 1 hour.

Next, referring to FIG. 35, sacrificial layer 802 is then partially removed using an etchant. The etchant passes through permeable polysilicon layer 803 in openings 804 to etch regions of sacrificial layer 802 underneath openings 804. The etch may, for instance, be performed with concentrated HF acid at 27° C. for 3 minutes. This etching step forms cavity 709 of shell 700.

The processed substrate 701 is then rinsed in DI water to remove all remaining HF acid. The rinse may be performed, for instance, for two hours.

Next, the processed substrate 701 is dried using, for example, a super-critical $CO_2$ process. This process is selected to prevent the permeable layer from cracking during drying.

Referring to FIG. 36, a sealing layer 806 is deposited over permeable layer 805 using LPCVD. The sealing layer may be, for instance, a 0.8 $\mu$m-thick layer of low-stress SiN. The process parameters for the deposition may be, for instance: 835° C., 140 mTorr, 100 sccm DCS, and 25 sccm $NH_3$. This step forms sealing structure 706 of shell 700 and may be omitted if the shell is intended for filtration purposes rather for forming a hermetic seal.

Next, referring to FIG. 37, openings 708 are then photolithographically defined and plasma etched through sealing layer 806, permeable layer 805, frame layer 803, and sacrificial layer 802. The plasma etch may be performed, for instance, with a $SF_6$ plasma at a chamber pressure of 150 mTorr, an RF power of 200 Watts, and a gas flow rate of 80 sccm for 10 minutes.

Finally, also referring to FIG. 37, a metallization layer 808 may optionally be deposited and defined over sealing layer 806 by processes commonly known in the art. This step forms metallization structure 707 of shell 700.

Combinations of materials different from those described above may be used to fabricate shells 500 and 700. For instance, sacrificial layers 602 and 802 may be composed of LTO, frame layers 604 and 803 may be composed of undoped polysilicon, and permeable layers 606 and 805 may be composed of in-situ doped polysilicon.

The present invention has been described in terms of representative embodiments. The invention, however, is not limited to the embodiments depicted and described. Rather, the scope of the invention is defined by the appended claims.

What is claimed is:

1. A microfabricated filter, comprising:
   a frame structure having a plurality of openings therethrough; and
   a permeable polycrystalline silicon membrane disposed over said plurality of openings in said frame structure.

2. The microfabricated filter of claim 1, wherein said permeable polycrystalline silicon membrane is formed using thin film deposition processes exclusively.

3. The microfabricated filter of claim 1, wherein said permeable polycrystalline silicon membrane has a thickness of between about 0.05 micrometers and about 0.3 micrometers.

4. A microfabricated filter, comprising:
   a permeable polycrystalline silicon thin film membrane having a surface, wherein said permeable polycrystalline silicon thin film membrane is permeable along a direction perpendicular to said surface; and
   a frame adapted to receive the permeable polycrystalline silicon thin membrame.

5. The microfabricated filter of claim 4, wherein said permeable polycrystalline silicon thin film membrane has a thickness of between about 0.05 micrometers and about 0.3 micrometers.

6. A microfabricated filter, comprising:
   a bulk substrate;
   a frame structure having a plurality of openings therethrough disposed over said bulk substrate;
   a permeable polycrystalline silicon membrane disposed over said frame structure;
   a cavity bounded by said bulk substrate and said frame structure; and
   a port coupled to said cavity.

7. The microfabricated filter of claim 6, wherein said permeable polycrystalline silicon membrane has a thickness of between about 0.05 micrometers and about 0.3 micrometers.

8. A microfabricated shell, comprising:
   a frame structure having a plurality of openings therethrough;

a permeable membrane disposed on said openings through said frame structure; and a cavity bounded by said frame structure.

9. The microfabricated shell of claim 8, wherein said permeable membrane is composed of permeable polycrystalline silicon.

10. The microfabricated shell of claim 9, wherein said permeable membrane has a thickness of between about 0.05 micrometers and about 0.3 micrometers.

11. The microfabricated shell of claim 8, wherein a microfabricated device is disposed within said cavity.

12. A microfabricated shell, comprising:

a bulk substrate;

a frame structure having a plurality of openings therethrough disposed on said bulk substrate;

a permeable membrane disposed on said openings through said frame structure;

a sealing structure disposed on said permeable membrane; and a cavity bounded by said bulk substrate and said frame structure.

13. The microfabricated shell of claim 12, wherein said permeable membrane is composed of permeable polycrystalline silicon.

14. The microfabricated shell of claim 13, wherein said permeable membrane has a thickness of between about 0.05 micrometers and about 0.3 micrometers.

15. The microfabricated shell of claim 13, wherein a microfabricated device is disposed within said cavity.

* * * * *

UNITED STATES PATENT AND TRADEMARK OFFICE
CERTIFICATE OF CORRECTION

PATENT NO. : 5,919,364  
DATED : July 6, 1999  
INVENTOR(S) : Lebouitz et al.

Page 1 of 1

It is certified that error appears in the above-identified patent and that said Letters Patent is hereby corrected as shown below:

Column 12, claim 15,
Line 13, change "13" to -- 12 --.

Signed and Sealed this

Twentieth Day of November, 2001

*Attest:*

*Attesting Officer*

NICHOLAS P. GODICI
*Acting Director of the United States Patent and Trademark Office*